United States Patent
Liu et al.

(10) Patent No.: US 6,974,528 B2
(45) Date of Patent: Dec. 13, 2005

(54) HIGH PERFORMANCE WIDE BORE ELECTROPHORESIS

(75) Inventors: Yaoqing Diana Liu, Millbrae, CA (US); James Jianmin Bao, Millbrae, CA (US)

(73) Assignee: Biomics, Inc., Newbury Park, CA (US)

( * ) Notice: Subject to any disclaimer, the term of this patent is extended or adjusted under 35 U.S.C. 154(b) by 193 days.

(21) Appl. No.: 10/205,579

(22) Filed: Jul. 24, 2002

(65) Prior Publication Data

US 2003/0052008 A1 Mar. 20, 2003

Related U.S. Application Data

(60) Provisional application No. 60/307,335, filed on Jul. 24, 2001.

(51) Int. Cl.$^7$ .................. G01N 27/447; G01N 27/453
(52) U.S. Cl. .................. 204/456; 204/451; 204/450; 204/600; 204/601; 204/621
(58) Field of Search .................. 204/621, 451, 204/452, 453, 454, 455, 601, 602, 603, 604, 605

(56) References Cited

U.S. PATENT DOCUMENTS

| | | | | |
|---|---|---|---|---|
| 4,305,799 A | * | 12/1981 | Schwarz et al. | 204/455 |
| 4,675,300 A | * | 6/1987 | Zare et al. | 204/452 |
| 4,911,808 A | * | 3/1990 | Hjerten | 204/452 |
| 5,015,350 A | * | 5/1991 | Wiktorowicz | 204/454 |
| 5,045,172 A | | 9/1991 | Guzman | 204/452 |
| 5,810,985 A | * | 9/1998 | Bao et al. | 204/451 |
| 5,906,724 A | * | 5/1999 | Sammons et al. | 204/627 |
| 6,063,251 A | * | 5/2000 | Kane et al. | 204/601 |
| 6,113,767 A | * | 9/2000 | Flesher et al. | 204/608 |
| 6,333,088 B1 | | 12/2001 | Le Febre et al. | 428/36.91 |

FOREIGN PATENT DOCUMENTS

EP 0576361 * 12/1993

* cited by examiner

Primary Examiner—Alex Noguerola
(74) Attorney, Agent, or Firm—Shirley Chen; Wilson Sonsini Goodrich & Rosati

(57) ABSTRACT

Methods, apparatus and systems are provided for efficient separation of various small and large molecules, especially biomolecules such as proteins, nucleic acids and polysaccharides. In particular, an electrophoresis apparatus is employed in a wide bore electrophoresis of samples in larger amounts than those in conventional capillary electrophoresis. The electrophoresis apparatus comprises: an electrophoresis chamber comprising a cathode, an anode and a housing; and a separation chamber positioned within the housing and comprising an inlet end, an outlet end, and one or more cooling capillaries positioned inside the separation chamber such that the longitudinal axis of at least one of the cooling capillaries is parallel to the direction of electric current flow from the anode to the cathode, wherein the end of the cooling capillary (or capillaries) is adapted to be coupled to a cooling device that allows cooling medium to pass through the cooling capillary. Electrophoresis systems incorporated with cooling mechanism can utilize wide bore separation tubes and tolerate much higher electric current than that in conventional CE systems. The apparatus can be used to separate and analyze a wide variety of molecules in an automatic, high throughput, and high performance manner. By using the apparatus, methods and systems, large amounts of biomolecules such as proteins can be separated with high resolution and in their native states. Samples separated by this system should be sufficient for many post-separation analyses by other techniques, such as mass spectrometry and crystallography. These features are especially advantageous in building and mining databases of biomolecules in functional genomics, structural genomics and proteomics in the post-genome era.

50 Claims, 15 Drawing Sheets

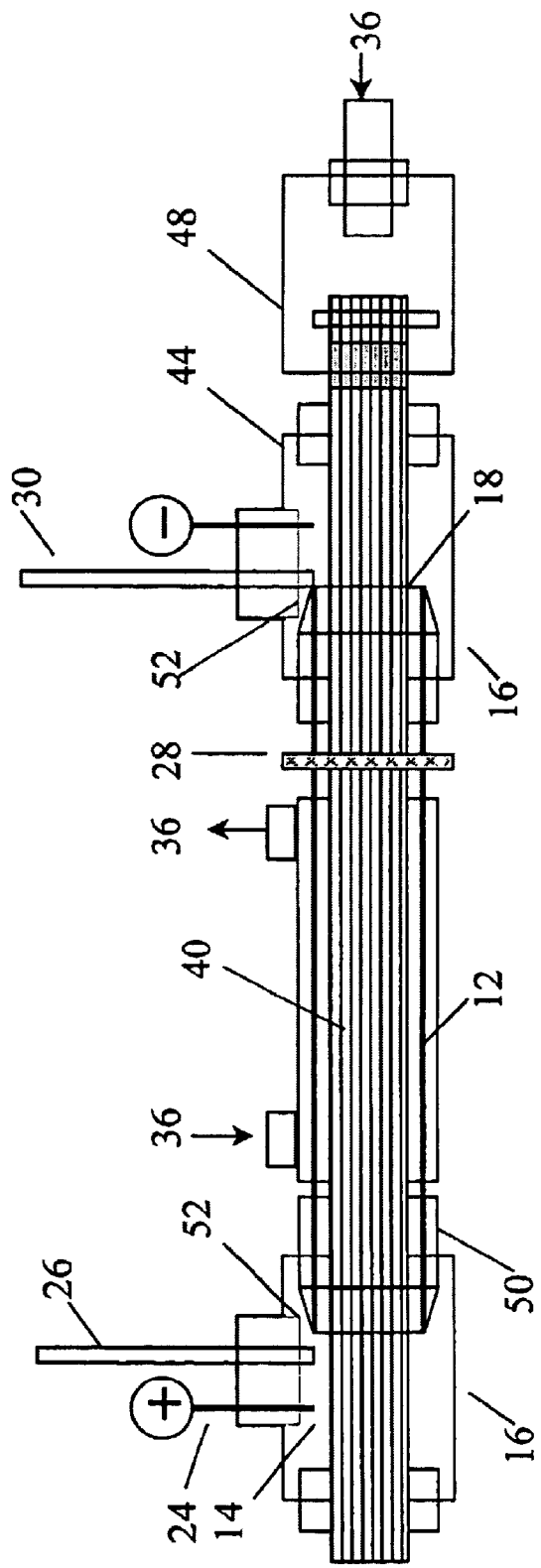

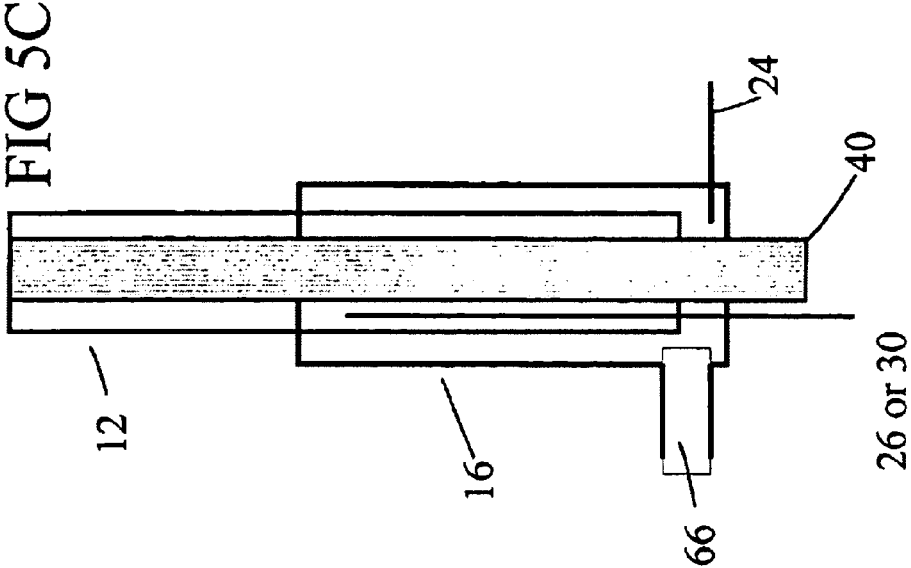
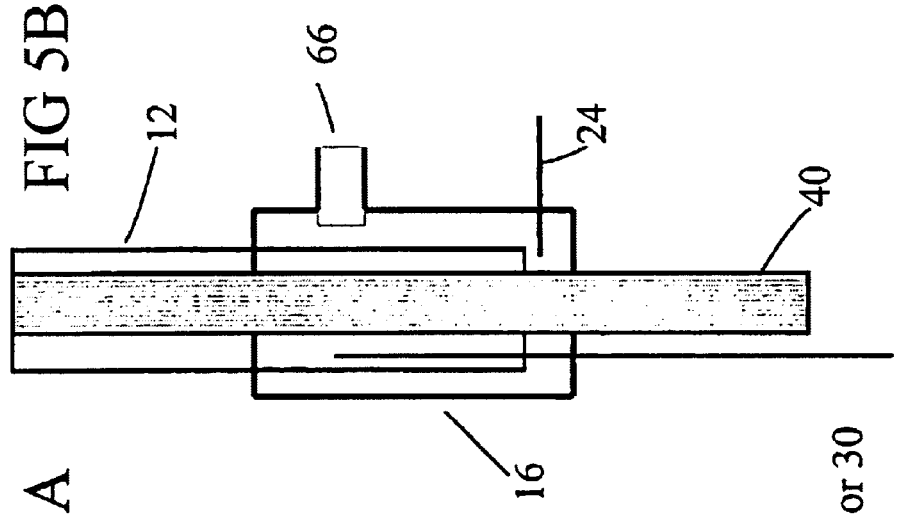
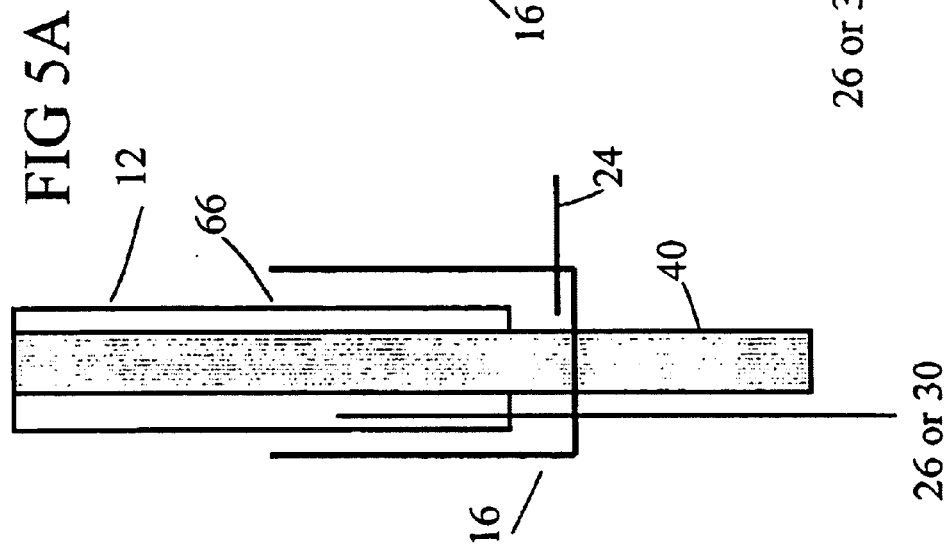

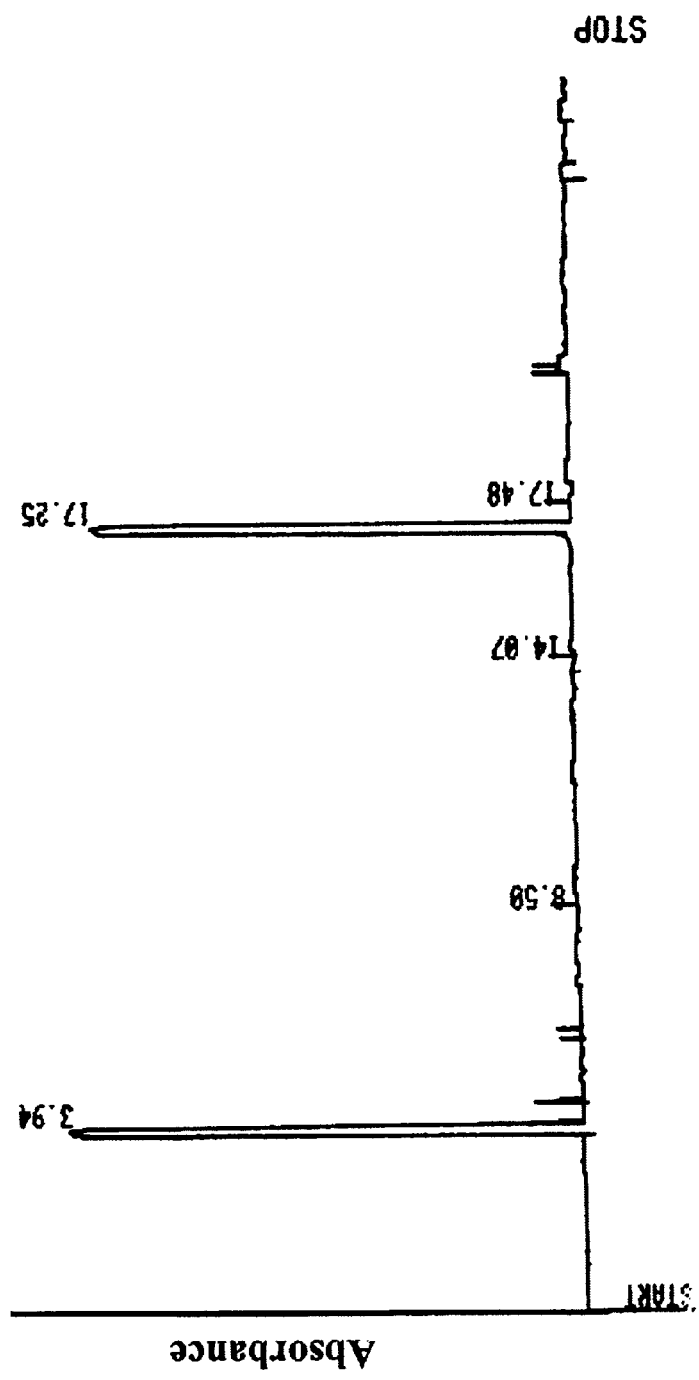
FIG 15  Separation of the Food Dyes

HIGH PERFORMANCE WIDE BORE ELECTROPHORESIS

CROSS REFERENCE TO RELATED APPLICATIONS

This application claims the benefit of U.S. Provisional Application Ser. No. 60/307,335 entitled "Interior heat sink for high performance electrophoresis apparatus" filed on Jul. 24, 2001. This application is incorporated herein by reference.

BACKGROUND OF THE INVENTION

1. Field of the Invention

The invention relates to apparatus, methods and systems for separation and analysis of samples by electrophoresis and more particularly to apparatus, methods, and systems for performing electrophoresis in a wide bore separation chamber such as a tube containing an interior heat sink formed by capillaries to break the interstices between the tube and the capillaries into multiple micro-channels for highly efficient separation of samples containing small and large molecules, especially biomolecules such as proteins, nucleic acids, and polysaccharides.

2. Description of the Related Art

Electrophoresis is a separation technique widely used in many field including biology, chemistry, food science, and forensic science, etc. Depending on the scale, electrophoresis can be classified as analytical and preparative electrophoreses. Analytical scale electrophoresis includes some of the most common formats, such as slab gel, capillary, and microchip based electrophoresis. The most common format of preparative scale electrophoresis is free flow electrophoresis (FFE, see M. C. Roman and P. R. Brown, Anal. Chem., 66 (1994) 86A). When large enough, slab gel electrophoresis can serve as a semi-preparative electrophoresis as well. Among all of these different formats of electrophoretic techniques, capillary electrophoresis (CE) is by far the most efficient separation technique, especially for biomolecules such as proteins, nucleic acids and polysaccharides. In addition, the throughput of the CE system can be significantly increased if multiple capillaries are placed in parallel to form capillary array electrophoresis (CAE). Typical examples of CE systems are described in U.S. Pat. No 4,898,658 (hereby incorporated by reference) while typical CAE systems are described in U.S. Pat. No. 5,730,850 and U.S. Pat. No. 5,582,705 (hereby incorporated by references).

Though CE has high efficiency in separating many compounds, especially biomacromolecules, such as proteins, DNA, and polysaccharides, the small ID of the capillary limits the amount of samples suitable for the system and thus severely impairs the usefulness of CE as a general tool to take advantage of the high efficiency of CE separations. Especially, the rapid development of proteomics and genomics demands new technologies that can handle the amount of samples beyond the reach of the current CE technique. Various attempts have been made to circumvent this problem.

The first approach was to use capillary bundles instead of a single capillary (see N. A. Guzman and L. Hernandez, in T. E. Hugli (Ed.), "Techniques in Protein Chemistry", Academic Press, San Diego, 1989, p.456; Fujimoto, C., Muramatsu, Y, Suzuki, M., Hirata, Y., and Jinno, K., Industrial Publishing and Consulting, Kobe, Japan, Sept. 11–14, 1990, pp. 684–692.). This approach was never popular because most of the current commercial CE instruments are not capable of handling capillary bundles. For example, the power supply in a typical CE lab is not suited for this purpose. Special instrumentation has to be made to accommodate this system. For most labs, the marginal gain from this approach does not justify the complexity involved. More importantly, it is hard to achieve exactly the same separation time in a large number of capillaries, and thus it's difficult to collect the same fractions from these multiple capillaries simultaneously. On the other hand, CAE systems do use multiple capillaries except these capillaries are totally independent of each other. Thus, CAE only increases the throughput of samples it can handle but does not change the amount of samples in each capillary.

The second approach is to use a relatively larger capillary with non-aqueous buffer, which generated much smaller current in the system (see S. P. Porras, M. Jussila, K. Sinervo, M.-L. Riekkola, Electrophoresis 20 (1999) 2510–2518). Unfortunately, non-aqueous CE method is not suited for many CE applications. Thus, the usefulness of this non-aqueous buffer approach is also very limited.

The third approach is to make restrictions at the two ends of a large capillary to reduce the actual current (see H. Yin, D. McManigill, C. A. Keely-Templin, R. R. Holloway, U.S. Pat. No. 5,658,446, hereby incorporated by reference; H. Yin, C. Keely-Templin, and D. McManigill, J. Chromatogr., A, 744 (1996) 45–54). This approach offers the potential of loading more samples into the system when a larger ID (180 $\mu$m) capillary is used. In the electrophoresis process, the buffer movement, and thus the current, is reduced due to the restrictions at the ends of the separation capillary. The reduced current will result in less Joule heat generation. However, it does not really improve any heat dissipation. This method is not very effective when the ID of the capillary is further increased.

Further, it is possible to reduce the current by packing the capillary with packing materials and use organic mobile phase. Chen et al. reported the use of 530 $\mu$m capillaries packed with 1.5 $\mu$m packing materials (see J-R. Chen, R. Zare, E. C. Peters, F. Svec, and J. J. Frechet, Anal. Chem. 73 (2001) 1987–1992). Most of the previous work can only extend the ID of capillaries up to 200 $\mu$m. The combination of packing column to reduce the effective ID and using organic solvents enabled this team to work with 500 $\mu$m capillaries. This is a significant progress in terms of the capillary size. However, clearly, this system can't be used as a general approach as it works only in a specific mode of CE (i.e. CEC) and needs to use organic solvent.

It is believed that without a better way of removing the excessive heat it would be difficult to increase the capillary size any further without a significant loss in separation efficiency.

In addition to not being able to handle relatively large amount of samples for separation, the current CE techniques have another major limitation. The fractions of the samples separated by CE can't be collected for subsequent analysis, which is critical to applications such as proteomics and genomics. Several teams have made attempts to collect fractions from CE (see R. A. Wallingford and A. G. Ewing, Anal. Chem., 59 (1987) 1762–1766; N. A. Guzman L. Hernandez, and B. G. Hoebel, Biopharm. 2 (1989) 2–37; O. Muller, F. Foret and B. L. Karger, Anal. Chem. 67 (1995) 2794). None of these methods is popular either because it is a very tedious process to collect anything meaningful from the nano-liter volume CE system or it takes too much effort to collect enough for any useful analysis. Further, collecting such a small volume of sample without dilution is very challenging.

The most practical approach to collect more samples is FFE. A typical FFE system with cooling can be found in U.S. Pat. No. 5,104,505 (hereby incorporated by reference). FFE is not a very popular electrophoresis system in analytical labs due to the fact that FFE is primarily a large scale preparative electrophoresis technique. It lacks the high efficiency of the most analytical electrophoresis systems and requires too much material, which makes FFE not suitable for many biological, especially proteomics applications. In addition, the separation efficiency is, even with cooling, relatively low as compared with that of CE technique.

The other common form of electrophoresis is slab gel electrophoresis, which is widely used in biochemistry as both analytical and semi-preparative techniques. Especially, by combing together two different modes of electrophoresis, such as the charge based isoelectric focusing (IEF) and size based gel separation, the two-dimensional (2-D) electrophoresis has been the method of choice for proteomics and genomics studies. Slab gel electrophoresis offers the advantages of parallel operation and direct comparison of samples. The sample requirement for slab gel is within a reasonable amount that most biochemistry labs can provide. The gel serves as the media that prevent convective movement in the system and help to enhance the various separations. Unfortunately, the current slab gel electrophoresis systems have their limitations as well. First, the gel used for the separation also reduces the efficiency in heat dissipation and thus limits the use of high electric field strength. Second, the relatively strong absorbance of the common gels prevents the direct detection of the analytes, such as proteins, DNA, and RNA, on the slab gels by UV absorbance. Third, the reagents, such as silver or Coomassie blue used to stain the gel for the determination of the analytes often fail to determine the quantity of the analytes, such as proteins. This is partially due to the inaccuracy in quantitating the stains themselves and partially due to the fact that the chemistry behind the staining is not very well understood. The staining molecules and the analytes do not have a known stoichiometric relationship.

Thus, there exists an urgent need for innovative strategies and instrumentation for carrying out separation and analysis of samples especially samples containing biomolecules, such as proteins, nucleic acids and polysaccharides, at certain amount with high performance and high throughput.

SUMMARY OF THE INVENTION

The present invention provides innovative methods, apparatus and systems for efficient separation of various small and large molecules, especially biomolecules such as proteins, nucleic acids and polysaccharides. In particular, the inventive methodology is employed in a wide bore electrophoresis of samples in larger amounts than those in conventional capillary electrophoresis (CE). One of the strategies taken in the present invention is to timely and efficiently remove the Joule heat from its origin during electrophoresis by employing an interior heat sink positioned within the separation chamber (e.g, a tube), thereby allowing different molecules in a large amount of samples to be separated with high resolutions under relatively high electric currents. Such an interior heat sink can be formed by putting together a plurality of capillaries designed to provide a large overall surface-to-volume ratio of the electrophoresis system and to break the big interstices between the separation tube and the capillaries into multiple micro-channels, thereby enhancing the cooling efficiency and resulting in a better tolerance to high currents. At the extreme, a single capillary with proper dimensions can also be used to achieve the same goal.

Compared with conventional electrophoresis techniques, the electrophoresis system in the present invention retains the high efficiency of separations as seen in CE and can be applied to nearly all areas where CE has been utilized. One of the significant advantages of the present invention, as compared with CE, is that the inventive electrophoresis system can perform similar separations with much larger amounts of samples. Further, the feasibility of forming parallel array renders this system comparable to slab gel electrophoresis in terms of parallel separations of multiple samples and yet more convenient in providing quantitative information of the analytes.

In addition to high separation efficiency and easy quantification, the inventive electrophoresis system can be adopted for gel-free electrophoresis and allows the separation and isolation of biomolecules in their native states, which is particularly important in analyzing biological samples. By combining the advantages of high separation efficiency, feasibility of free-solution, convenience for quantification of CE and the ability to handle a relatively large amount of samples and the feasibility of parallel separation in slab gel, the current inventive electrophoresis system offers the best of all and is the method of choice for the analyses of various biological samples. Further, this system can be integrated into a streamlined process of sample injection, separation, detection, isolation and analysis in an automatic, high throughput, and high performance manner. These features are especially advantageous in building and mining databases of biomolecules in functional genomics, structural genomics and proteomics in the post-genome era.

In one aspect of the invention, a separation chamber (e.g., a tube) is provided that contains an interior heat sink for efficiently dissipating the Joule heat from its origin. Such a separation chamber can be used in electrophoresis to separate and isolate molecules of interests, especially biomolecules such as proteins, nucleic acids and polysaccharides. In one embodiment, a separation tube is provided that comprises:

an inlet end;

an outlet end; and a plurality of capillaries positioned inside the separation tube such that the longitudinal axis of at least one of the capillaries is parallel to the longitudinal axis of the tube, and an interstice is formed between the interior of the separation tube and the exterior of the plurality of the capillaries to allow fluidic and material communications through the interstice.

The inner cross-sectional dimensions of the capillary and the separation tube can be as small as practically available as long as the inner dimensions of the separation tube is sufficiently large to accommodate the capillary or capillaries. For example, the inner cross-sectional dimension of the capillary and/or the separation tube can be as small as 1 nanometer or below, which may be facilitated by using a nanotube such as carbon nanotube. Preferably, the separation tube has an inner cross-sectional dimension of at least 100 micrometers.

The cross-section of the separation tube may adopt any shape, such as circular, rectangular, and square. Preferably, the cross-section of the tube is circular and its inner dimension (ID) is between 100–1,000,000 micrometers, more preferably 200–10,000 micrometers and most preferably 300–5,000 micrometers.

The separation tube may be made of any material, preferably electronically non-conductive material including but not limited to glass, quartz, fused silica, and polymers such as Teflon®, polycarbonate, polymethylmethacrylate (PMMA) or silicone. The interior of the separation tube may be coated with different material to change the surface properties for specific applications. For example, it is a common practice to coat the surface with a hydrophilic layer, such as polyacrylamide, to shield the interaction between the surface and the analytes (i.e. proteins).

According to the embodiment, the cooling capillary may have a length preferably longer than but can be equal to or shorter than that of the tube. The cross-section of the capillary may adopt any shape, such as circular, rectangular, and square. Preferably, the cross-section of the capillary is circular and its ID is between as small as practically available to 1,000 micrometers, more preferably 50–500 micrometers and most preferably 100–400 micrometers; and the outer dimension (OD) is between as small as practical to 1500, more preferably 50–1000 micrometers and most preferably 100–500 micrometers.

The capillary may be made of any thermally conductive material, preferably also electronically non-conductive material including but not limited to glass, quartz, fused silica, and polymers such as Teflon®, polycarbonate, polymethylmethacrylate (PMMA) or silicone. The exterior of the capillary may be coated with different material to change the surface properties for specific applications. For example, it is a common practice to coat the surface with a hydrophilic layer, such as polyacrylamide, to shield the interaction between the surface and the analytes (i.e. proteins).

The capillaries may adopt the same or different dimensions. Preferably, the capillaries adopt substantially the same ID and OD.

In addition to the capillaries, one or more relatively larger solid rods, open tubes, or both, which are dimensioned properly may also be positioned parallel to the longitudinal axis inside the separation tube, especially for large separation tubes. These solid rods and/or open tubes break the interior of the separation tube into one or more large tunnels, within which the capillaries can be positioned to further break these tunnels into smaller capillary channels.

The cross-section of the solid rods and/or open tubes inside the separation tube may adopt any shape, such as circular, rectangular, and square. Preferably, the cross-section of these rods and tubes is circular and their ODs substantially smaller than that in the separation tube.

These rods and/or open tubes may be made of any material, preferably electronically non-conductive material including but not limited to glass, quartz, fused silica, and polymers such as Teflon®, polycarbonate, polymethylmethacrylate (PMMA) or silicone. The exterior of these rods and/or tubes may be coated with different material to change the surface properties for specific applications. For example, it is a common practice to coat the surface with a hydrophilic layer, such as polyacrylamide, to shield the interaction between the surface and the analytes (i.e. proteins).

Optionally, when the separation tube is circular in cross-section with an internal radius R and the capillaries are circular in cross-section with substantially the same IDs and ODs, and no other structural components such as the solid rods and/or open tubes, the number of the capillaries (n) is n or fewer, such as n-1, or n-2, etc, as determined based on the general formula:

$$\frac{S}{V} = \frac{2(R+nr)}{(R^2-nr^2)}.$$

where S/V is the overall surface-to-volume ratio of the electrophoresis system including both the separation tube and the plurality of capillaries, R is the internal radius of the separation tube, and r is an average OD of the capillaries. Preferably, S/V is 1–500, more preferably 40–200. When R is between 100–5,000 micrometers, r is preferably between 20–500 micrometers, and more preferably 50–300 micrometers.

If the capillaries are circular in cross-section with different ODs, the number of the capillaries, n, and the S/V has a more general relationship, i.e., $$\frac{S}{V} = \frac{2\left(R+\sum_{i=1}^{n}r_i\right)}{\left(R^2-\sum_{i=1}^{n}r_i^2\right)}.$$

It should be noted that while a plurality of capillaries is preferred to construct the cooling capillaries, a single capillary is also contemplated to cool the system from within the separation tube. Depending on the interior dimension of the separation tube, the single capillary may adopt a specific size and shape to achieve the goal of providing sufficient cooling for efficient separation of analytes in a sample.

When a plurality of capillaries is used to construct the separation tube, the capillaries can be arranged and positioned inside the separation tube such that the interstices between the interior of the separation tube and the exterior of the plurality of the capillaries form many micro channels, mimicking multiple open capillaries. The number, shape, and cross-sectional dimensions of these channels in the interstices may vary based on the size and geometry of the separation tube and the sizes, geometry, and number of capillaries and, if any, the structural materials such as rods and tubes, involved in forming the interstices. While the specific dimensions of a particular micro channel may depend on the closeness of adjacent capillaries as well as the separation tube, the average cross-section dimensions of these micro channels is preferably less than 200 micrometer, more preferably less than 100 micrometer, and most preferably less than 75 micrometer to enhance the efficiency of removing Joule heat from these micro channels.

It is contemplated that the interstices between the separation tube and the plurality of capillaries also determine the total volume available for sample separation. This volume is related to the size and geometry of the separation tube, the size, shape, and number of the plurality of capillaries. Specifically, this volume is restricted by its relationship with other parameters (R, r, n) as shown in the equation provided above. In general, a larger volume is desired for better detection and analysis. However, the amount of sample, especially biological samples, is limited by its sources and preparation procedures. Therefore, it is necessary to find a balanced between desired amount and the available amount. For biological samples, the desirable volume of sample for each analysis is preferably 5–50,000 nano-liter (nL), more preferably 50–10,000 nL, and most preferably 100–5,000 nL. Thus, it is believed that the size of the separation tube and the capillary as well as the number of the capillaries should be carefully considered before a system is constructed. Among all of these parameters, the single most important parameter is believed to be the size of the capillary, r, which ultimately determines the size of the micro-channels in the interstices among these capillaries.

In another aspect of the invention, an electrophoresis apparatus is provided for efficient separation and isolation of various molecules, preferably biomolecules. In one embodiment, the electrophoresis apparatus comprises:

an electrophoresis chamber comprising a cathode, an anode and a housing; and a separation chamber positioned within the housing and comprising an inlet end, an outlet end, and one or more cooling capillaries positioned inside the separation chamber such that the longitudinal axis of at least one of the cooling capillaries is parallel to the direction of electric current flow from the anode to the cathode, wherein the end of the cooling capillary (or capillaries) is adapted to be coupled to a cooling device that allows cooling medium to pass through the cooling capillary.

According to the embodiment, the separation chamber may adopt any shape or size. For example, the separation chamber may be a tube, a square or a rectangular box (e.g., the one used in slab gel electrophoresis). Preferably, the separation chamber is a tube with a circular cross-section and an ID between 100–1,000,000 micrometers, more preferably 200–10,000 micrometers and most preferably 300–5,000 micrometers.

The separation chamber may be made of any material, preferably electronically non-conductive material including but not limited to glass, quartz, fused silica, and polymers such as Teflon®, polycarbonate, polymethylmethacrylate (PMMA) or silicone. The interior of the separation chamber may be coated with different material to change the surface properties for specific applications. For example, it is a common practice to coat the surface with a hydrophilic layer, such as polyacrylamide, to shield the interaction between the surface and the analytes (i.e. proteins).

According to the embodiment, the cooling capillary may have a length preferably longer than but can be equal to or shorter than that of the tube. The cross-section of the cooling capillary may adopt any shape, such as circular, rectangular, and square. Preferably, the cross-section of the capillary is circular and its ID is between as small as practically available to 1,000 micrometers, more preferably 50–500 micrometers and most preferably 100–400 micrometers; and the outer dimension (OD) is between as small as practical to 1500, more preferably 50–1000 micrometers and most preferably 100–500 micrometers.

The cooling capillary may be made of thermally conductive and electronically non-conductive material including but not limited to glass, quartz, fused silica, and polymers such as Teflon®, polycarbonate, polymethylmethacrylate (PMMA) or silicone. The exterior of the capillary may be coated with different material to change the surface properties for specific applications. For example, it is a common practice to coat the surface with a hydrophilic layer, such as polyacrylamide, to shield the interaction between the surface and the analytes (i.e. proteins).

According to the embodiment, the separation chamber may further comprise one or more solid rods and/or open tubes positioned inside the separation tube. One or both ends of the solid rods or open tubes may be adapted to be coupled with the cooling device. The cross-section of the solid rods or open tubes may adopt any shape, such as circular, rectangular, and square. Preferably, the cross-section of the solid rod or open tube is circular and the OD thereof substantially smaller than the ID of the separation chamber. The solid rods and/or open tubes are preferably positioned in a relatively large separation chamber.

The solid rods or the open tubes may be made of any material, preferably electronically non-conductive material including but not limited to glass, quartz, fused silica, and polymers such as Teflon®, polycarbonate, polymethylmethacrylate (PMMA) or silicone. The exterior of these rods and/or tubes may be coated with different material to change the surface properties for specific applications. For example, it is a common practice to coat the surface with a hydrophilic layer, such as polyacrylamide, to shield the interaction between the surface and the analytes (i.e. proteins).

The separation chamber may further comprise gel or other additives capable of conducting electrophoresis. These gel and additives included but not limited to agarose, polyacrylamide, and other polymeric materials like polyethylene glycol, the concentration of which may depend on chemical characteristics and the molecular weights of the analytes in the sample to be analyzed.

Also according to the embodiment, the electrophoresis apparatus may further comprise a cooling device coupled to either one or both ends of the cooling capillary (or capillaries).

The cooling device may comprise a cooling reservoir containing any cooling medium, for example liquid coolant such as chilled water, water-glycerin solution, liquid nitrogen, fluorochemicals, solid coolant such as ice and dry ice, and gaseous coolant such as air, nitrogen gas, ammonia, and carbon dioxide. The cooling device may further include a pump to pump the cooling medium through the cooling capillary and circulate the cooling medium through the cooling device. Optionally, the cooling device may include a compressor such as the one used in an air conditioner or a refrigerator to compress the cooling medium to liquid first, then allow the liquid cooling medium to pass through and evaporate within the cooling capillaries.

The cooling device may be coupled to the cooling capillary through a connector. For example, an inlet connector can be attached to one end of the cooling capillary to allow the cooling device to cool the capillary. Alternatively, an inlet and an outlet connector may be attached to the two ends of the cooling capillary respectively to allow recycling of the coolant through the cooling device. Preferably, the inlet connector has a mechanic strength tolerable to a pressure of at least 10 psi, more preferably 100 psi, and most preferably 1000 psi. For example, the inlet connector may be a metal union with two ends (male or female) with one of them connected to the cooling device, which is at high pressure generated by a high-pressure pump (e.g., an HPLC pump) and the other end connected to one of the two ends of the cooling capillary. The outlet connector may have the same mechanic strength as or weaker than the inlet connector.

Optionally, a seal may be used at the junction between the inlet and/or outlet connector and the cooling capillary to prevent leakage of coolant. The seal may be made of any sealant capable of blocking leakage of materials, including but not limited to rubber, vacuum grease, liquid sealant, and epoxy-type glues.

Optionally, the apparatus may further comprise a first buffer reservoir and a second buffer reservoir coupled to the cathode and anode, respectively. For example, the first buffer reservoir may be positioned immediately adjacent to the inlet end of the separation chamber, and the second buffer reservoir immediately adjacent to the outlet end of the separation chamber.

Optionally, the apparatus may further comprise an exterior heat sink configured to contact the exterior surface of the separation chamber to further cool down the tube during electrophoresis. The exterior heat sink may be a liquid bath in which the separation chamber is immersed. The liquid bath may be coupled to a thermo-electrical cooling sink to exert the cooling effects on the separation chamber. Optionally, the cooling device and the exterior heat sink may share the same coolant and the same pumping system. Preferably, the coolant is pumped through the cooling capillaries first and then through the exterior heat sink.

Alternatively, the exterior heat sink may be a metal heat sink to irradiate heat from the separation chamber, an example of which is described in U.S. Pat. No: 6,103,081.

Also optionally, the apparatus may further comprise an injection device for introducing a sample into the separation chamber and subject to electrophoresis. The injection device is coupled to the inlet end of the separation chamber and the sample may be introduced to the tube by any mode of injection, including but not limited to hydrodynamic injection and electrokinetic injection.

The injection device may also be coupled to the inlet end of the separation chamber through a sampling line inserted into the separation chamber. The sample may be injected by manual injection via a syringe or by an autosampler. Preferably, the sampling line is a capillary with an ID of 10–1000 micrometers.

Alternatively, the injection device may be coupled to the inlet end of the separation chamber through a small channel created near the inlet end of the separation chamber, for example by attaching a T or cross union to the inlet end. The sample may be injected by manual injection via a syringe or by an autosampler through one of the openings of the union while the rest of the openings may be coupled to the cooling capillaries. Also optionally, the electrophoresis apparatus may further comprise a power supply, preferably a high voltage power supply, which provides at least 1 milliampere of electric current during electrophoresis.

Also optionally, the electrophoresis apparatus may further comprise a detection device for detecting the presence and/or amount of analytes in the sample during electrophoresis. The detection device may include a light source and a light-sensing device, such as a photodiode or photo multiplier tube (PMT). The light source may be a UV-Vis light source and/or a laser and the separation chamber may be positioned near the light source and the light-sensing device, which can detect transmission, reflection, and scattering lights from the light source when it is placed at different positions. For UV-Vis detection, the detector is positioned in the side of the separation tube opposite to the light source and the light transmitted though the separation tube is detected. If the separation chamber is not UV-Vis-transparent, the separation may include a detection window to allow the light to be transmitted to the analytes in the sample. Alternatively, if fluorescence is detected, the detector can be placed in any place but preferably in a position, which forms a 90-degree angle relative to the light source with the separation tube at the corner. To enhance the intensity of the fluorescence, a laser may be introduced to the separation chamber.

Optionally, scatter light can also be detected if no suitable chromophors are available.

Optionally, the detection device may further include a first fiber optics to transmit light to the separation chamber and a second fiber optics to receive light emitted from the analytes in the sample. For example, in one embodiment, both of the first and second fiber optics may be a 400-micrometer core, UV-transmittable fiber optical cables. It is noted that either the first or the second fiber optics may be used without the other one.

The detection device may be coupled to the outlet end of the separation chamber to detect the separated analytes released therefrom. Such a post-separation mode of detection may be adopted to avoid creating a detection window on the separation chamber that is not UV-Vis transparent. Preferably, to prevent diffusion of the analytes the separation chamber further comprises a detection tube (e.g., a capillary) coupled to the outlet end of the chamber. The detection capillary may be UV-Vis transparent itself or capable of guiding the analytes in the separation buffer from the separation tube into a flow cell for detection.

Also optionally, the outlet end of the separation chamber is adapted to be coupled to a sample collector such that fractions of analytes from the sample can be collected for further uses. The sample collector may be a manual or an automatic collector that may be capable of controlling the mode of collection in response to signals from a detection device used to monitor the analytes in the sample. Optionally, the sample collector and the detection device may be consolidated into a single system.

Also optionally, the outlet end of the separation chamber is adapted to be coupled to an analytical instrument for further characterization of the analytes in the sample that are separated by electrophoresis. Examples of the analytical instrument include, but are not limited to, instruments for mass-spectroscopy, nuclear magnetic resonance (NMR) spectroscopy, crystallography, chromatography, and electrophoresis.

In yet another aspect of the invention, an electrophoresis apparatus is provided for high throughput separation of multiple samples. In one embodiment, the electrophoresis apparatus comprises:

an electrophoresis chamber comprising a cathode, an anode and a housing; and a plurality of separation chambers positioned within the housing, each of the separation chambers comprising an inlet end, an outlet end, and one or more cooling capillaries positioned inside each of the separation chamber such that the longitudinal axis of at least one of the cooling capillaries is parallel to the direction of electric current flow from the anode to the cathode, wherein the end of the cooling capillaries is adapted to be coupled to a cooling device that allows cooling medium to pass through the cooling capillaries. According to the embodiment, the plurality of separation chambers may be positioned within the housing such that each of the outlet ends of the chambers is positioned to release the analytes from the sample to a well of a multi-well plate, such as a 96-, 384-, or 1536-well plate.

Also according to the embodiment, the plurality of the separation chambers may share a common buffer reservoir or have separate buffer reservoirs for each separation chamber. The electrophoresis can share common anode and cathode electrodes or have the electrodes controlled individually.

Further according to the embodiment, the plurality of the separation chambers may share a common detector or have separate detector for each tube.

In yet another aspect of the invention, an apparatus is provided for separation of samples within channels on a flat surface platform, for example on a microchip. In one embodiment, an electrophoresis apparatus is provided that comprises:

a substantially planar structure;

one or more separation channels formed in the planar structure, each of the separation channels having first and second ends that are coupled to and in fluid communication with first and second buffer reservoirs, respectively, and coupled to an anode and a cathode;

one or more cooling capillaries positioned inside the one or more separation channels such that the longitudinal axis of at least one of the cooling capillaries is parallel to the planar surface of the structure, wherein the end(s) of the one or more cooling capillaries is adapted to be coupled to a cooling device that allows cooling medium to pass through the cooling capillaries.

When there are two or more separation channels in the structure, the separation channels may be in fluid communication with each other, for example, through a junction T positioned between one end of one separation channel and a middle point of another channel or a junction Cross between some middle points of both separation channels. The separation channel may make turns, which are created by allowing two separation channels positioned at an angle (not 180°) to have fluidic communication at a position between the first and second ends of the separation channels.

The first (or second) reservoirs coupled to the separation channels may be the same or independent from each other. The anodes (or cathode) coupled to the separation channels may be the same or independent from each other. The first and second buffer reservoirs may be fabricated on the surface of the structure in multiple positions. When there are two or more separation channels each with cooling capillaries, the ends of the cooling capillaries in these separation channels may be coupled to a common cooling device. Each of the cooling capillaries may be individually coupled to the cooling device, or connected with each other via a connector linking the ends of the capillaries, thus forming a cooling network laid out along the planar surface or multidimenion of the structure.

The electrophoresis apparatus may be adapted to be coupled with a common detector or a separate detector for each separation channel. Alternatively, a two-dimensional detection device, such as charge coupled device (CCD) can image the whole surface plane.

The width of the separation channel is preferably between about 10–10,000 micrometers, more preferably 50–5,000 micrometers, and most preferably 500–1,500 micrometers.

In yet another aspect of the invention, an electrophoresis system is provided for continuous separation of multiple samples simultaneously in multiple dimensions. In one embodiment, the electrophoresis system comprises:

a first electrophoresis chamber comprising a first cathode, a first anode, and a first housing;

a first separation chamber positioned in the first housing and having a first inlet and outlet end;

a second electrophoresis chamber comprising a second cathode, a second anode and a second housing;

a second separation chamber positioned in the second housing and having a second inlet and outlet end; and a plurality of cooling capillaries positioned in the first and/or second separation chamber such that the longitudinal axis of at least one of the cooling capillaries is perpendicular to the direction of electric current flow from the first (or second) anode to the first (or second) cathode, wherein the first inlet end of the first separation chamber is coupled to a means for pressuring a sample to move through the interstices formed between the interior of the first or second separation chambers and the exterior of the plurality of cooling capillaries; and the end(s) of the cooling capillaries are coupled to a cooling device that allows cooling medium to pass through the cooling capillaries.

According to the embodiment, the first outlet end of the first separation chamber is coupled to the second inlet end of the second separation chamber to allow fluid communication between them.

Also according to the embodiment, the first (or second) separation chamber may further comprise two buffer reservoirs coupled to the first anode and first cathode, respectively.

Also according to the embodiment, the first anode and cathode are electrically independent from the second anode and cathode. The second anode and cathode can be parallel or perpendicular to the first anode and cathode.

Also according to the embodiment, the first and/or second separation chamber may be adapted to be coupled to a detection device. Optionally, only the second separation chamber is adapted to be coupled to a detection device.

In yet another aspect of the invention, methods are provided for high performance separation of analytes in a sample by electrophoresis. In one embodiment, the method comprises the steps of:

providing an electrophoresis apparatus which comprises an electrophoresis chamber comprising a cathode, an anode and a housing, and a separation chamber positioned within the housing and comprising an inlet end, an outlet end, and one or more cooling capillaries positioned inside the separation chamber such that the longitudinal axis of at least one of the cooling capillaries is parallel to the direction of electric current flow from the anode to the cathode, wherein the end of the cooling capillary is adapted to be coupled to a cooling device;

applying an electrophoretic potential to the inlet end and the outlet end of the separation chamber;

delivering cooling medium inside the cooling capillaries through the cooling device; and cooling the separation chamber through the cooling capillaries during the electrophoresis.

Optionally, the method may further comprise the step of detecting the presence and/or amounts of the analytes in the sample. The analytes may be detected while contained in the separation chamber or after released from the outlet end of the separation chamber.

In a particular embodiment, the separation chamber is a separation tube. When the analytes are detected after released from the outlet end of the separation tube, a detection tube (e.g., a detection capillary) may be coupled to the outlet end of the separation tube. Optionally, a potential may be applied to the detection tube to reduce the diffusion of the analytes being released from the separation chamber. This detection potential also reduces the resistance of flow in the detection tube. It is contemplated that in order to determine the proper potential on the detection tube, it may be necessary to obtain the flow resistances within the separation tube and the detection tube.

When the separation tube is directly connected to the detection tube, the flow rate, F, is the same in both segments. Depending on the specific situation, the flow rate F is related to the applied potential V, the mobility of the flow in each segment, the lengths of the two segments and the cross section areas.

In one variation, the electrophoretic potential and the detection potential are applied serially such that the voltage at the inlet end of the separation tube is the highest; the voltage at the outlet end of the separation tube lower and the voltage at the exit of the detection tube lowest. This may be facilitated by using a single power supply to apply the high voltage at the inlet of the separation tube and the grounding at the exit of the detection tube while the outlet of the separation tube has a potential somewhere between these two points. Optionally, a first and second power supplies may be used with the first power supply applying the high voltage at the inlet end and grounding on the outlet end of the separation tube, and the second power supply sharing the same common but providing a negative high voltage to the exit end of the detection tube. The total resistance of the separation tube and the detection tube can be determined based on the general formula:

$$R = \frac{l_1}{\mu_1 S_1} + \frac{l_2}{\mu_2 S_2}$$

where $l_1$ and $l_2$ are the lengths of, $S_1$ and $S_2$ the intersection areas of, and $\mu_1$ and $\mu_2$ the mobility of the buffer in the separation tube and the detection tube, respectively.

In another variation, the electrophoretic potential and the detection potential are applied in parallel. This may be facilitated by using a first and second power supplies sharing the same common at the outlet point of the separation tube while the high voltages of the first and second power supplies are applied to the inlet of the separation tube and the exit of the detection tube, respectively. The total resistance of the separation tube and the detection tube can be determined based on the general formula:

$$\frac{1}{R} = \sum_{i=1}^{n} \frac{1}{R_i} = \sum_{i=1}^{n} \frac{\mu_i S_i}{l_i}$$

where n equals 2, $l_1$ and $l_2$ are the lengths of, $S_1$ and $S_2$ the intersection areas of, and $\mu_1$ and $\mu_2$ the mobility of the buffer in the separation tube and the detection tube, respectively. It should be noted that when multiple separation tubes are included in the electrophoresis apparatus, n may be an integer larger than 2, such as 4, 16, 80, 100, etc.

Also optionally, the method may further comprise the step of collecting the analytes in the sample separated by the electrophoresis. The collected analytes may be subjected to further analysis such as mass-spectroscopy, nuclear magnetic resonance (NMR) spectroscopy, crystallography, chromatography, and electrophoresis.

According to any of the above apparatus and methods, the sample may contain small molecules such organic molecules, dyes, sugar, oligosaccharides, polysaccharides, deoxyribonucleosides and analogs, ribonucleosides and analogs, deoxyribonucleotides and analogs, ribonucleotides and analogs, oligonucleotides, DNAs, RNAs, amino acids, peptides, proteins, antibodies, and radio-isotope or fluorescence-labeled molecules thereof. The sample may be in a form of solution, suspension, cell lysate, and homogenized tissue. The sample may be obtained from laboratory preparations or directly from a clinical sample such as a biopsy, a blood sample, and samples of other body fluids.

BRIEF DESCRIPTION OF THE FIGURES

FIG. 2 is a detailed view of the basic configuration of the separation cartridge containing the separation tube incorporated with the cooling capillaries as well as the exterior cooling.

FIG. 5 shows some more alternative reservoirs allowing the end of the separation tube in vertical position: A) an open U-shape, B) a closed box with an opening on the side, and C) an L-shape.

FIG. 10C shows the traces of samples following the combined forces of the electric force and the flow force.

FIG. 14 shows the Ohm plots with simultaneous cooling of both the interior and the exterior of the separation tube.

FIG. 15 is an electropherogram showing the separation of the components of a McCormick green food color.

DETAILED DESCRIPTION OF THE INVENTION

Figure 1:
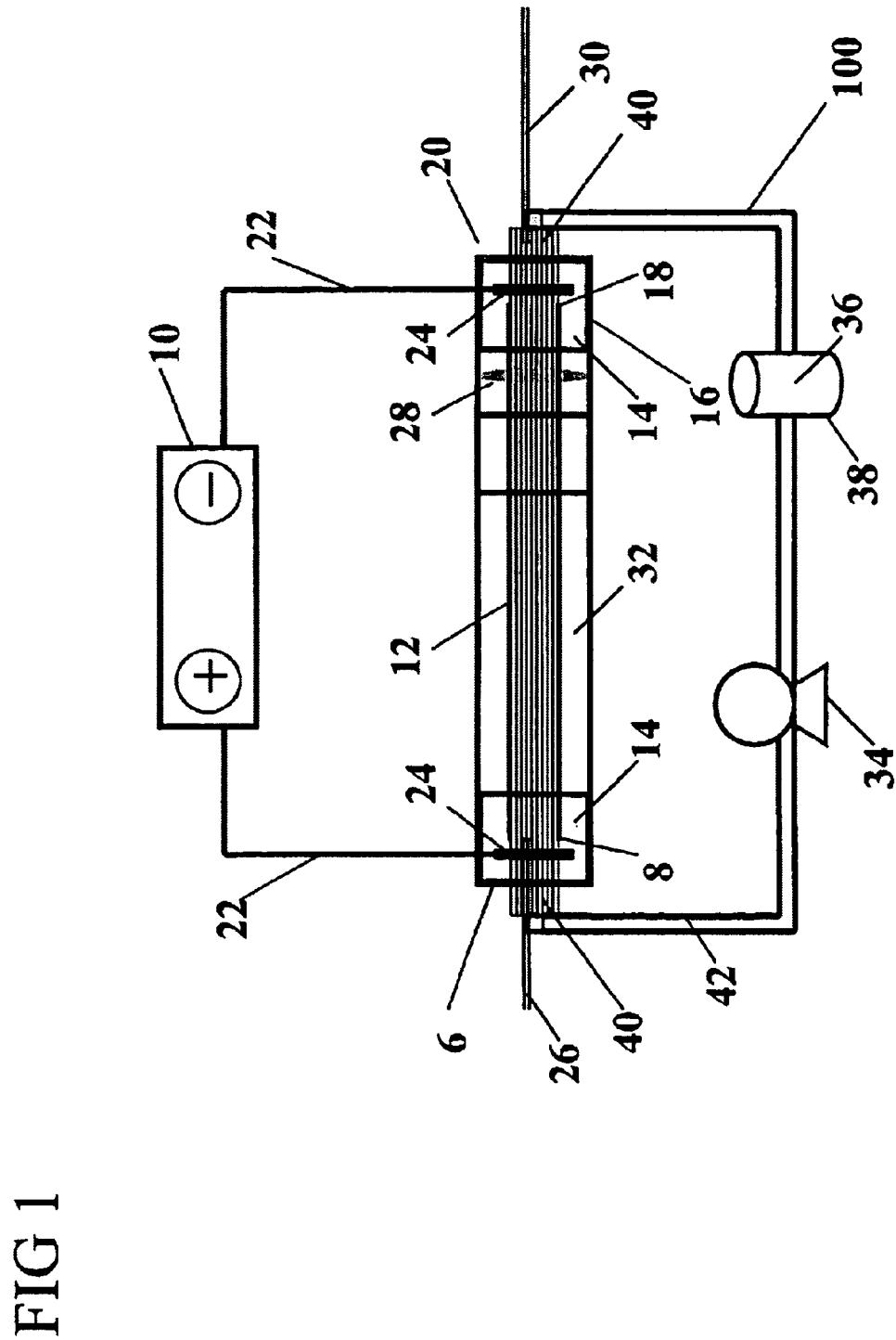
FIG. 1 schematically depicts a typical wide bore electrophoresis system incorporated with interior cooling of the separation tube.

The present invention provides innovative methods, apparatus and systems for efficient separation of various molecules, especially biomolecules such as peptides, proteins, nucleic acids and polysaccharides. In particular, a high performance wide bore electrophoresis (HPWBE) system is provided that is capable of performing electrophoresis with high separation efficiency for larger amounts of samples than in a conventional CE system.

According to the present invention, the wide bore electrophoresis system is capable of handling significantly larger amount of samples than that in a typical CE system. In general, the amounts of samples are in the sub-micro liter or more scale, which is at least 100 folds or more than that in a typical CE system (nano-liter scale). Still, these amounts of samples are readily obtainable from most biological systems. With increased amount of samples, the wide bore electrophoresis system will be compatible with other techniques such as mass spectrometry (MS) and nuclear magnetic resonance (NMR) techniques. This compatibility will facilitate online structural identification of the analytes separated by the electrophoresis process.

Also according to the present invention, the Joule heat generated during the electrophoresis process is efficiently removed by the addition of the interior cooling to the system. As expected, the current in the wide bore electrophoresis system is significantly higher than that in a typical CE system. This increase could be hundreds or even more folds if the ID of the wide bore tube is large enough. By incorporating an interior cooling into the system, the invention significantly improves the ability of the system to dissipate Joule heat. Especially, when the cooling capillaries are small enough that the interstices among multiple capillaries are significantly small forming multiple capillary channels with small IDs. Since these capillaries are surrounded with multiple capillaries containing moving coolant inside, the heat generated can be removed immediately before it accumulates, i.e. the present invention removes the Joule heat from its origin. Optionally, an outside coolant surrounding the separation tube can be used for further enhancing the cooling efficiency.

The above-described inventive strategy for HPWE can be implemented by using an electrophoresis system with the present invention. In one embodiment, the electrophoresis apparatus comprises:

an electrophoresis chamber comprising a cathode, an anode and a housing; and a separation chamber positioned within the housing and comprising an inlet end, an outlet end, and one or more cooling capillaries positioned inside the separation chamber such that the longitudinal axis of at least one of the cooling capillaries is parallel to the direction of electric current flow from the anode to the cathode, wherein the end of the cooling capillary (or capillaries) is adapted to be coupled to a cooling device that allows cooling medium to pass through the cooling capillary.

According to this embodiment, one or more open capillaries are inserted inside an electrophoresis system. Proper coolant can pass through the open capillaries and carry out heat transmitted into the capillaries from the electrophoresis system. The coolant can be either gas and/or liquid at room or lower temperature. Typical coolants (or refrigerants) include, but not limited to, water, oil, fluorochemicals, such as R12 and/or R234a, ammonia, carbon dioxide, methyl chloride, methylene chloride, sulfur dioxide, etc. A pump or compressor may be involved to drive the coolant pass through the cooling capillaries. While passing through these capillaries, the coolant will carry away the excessive heat generated during the electrophoresis process. In addition to interior cooling, proper cooling from outside can also be incorporated to enhance the effectiveness of the cooling. While the present invention contemplates a variety of materials, fused silica capillary is chosen in this description, as it is lightweight, is readily available from commercial manufacturers, and is an excellent heat conductor.

Also according to the embodiment, samples may be introduced into the separation chamber by using an injector or an autosampler. Due to the relatively large amount of sample volume, as compared with CE, for the wide bore electrophoresis system, the samples can be directly injected using most commercial autosamplers. Alternatively, samples can also be introduced into the separation tube through the traditional ways as in CE, i.e. pressure from the sample vials, vacuum from the outlet end, or electro-kinetic injection, etc. Further, samples can also be directly injected into the separation tube through a syringe.

Also according to the embodiment, the separated analytes can be detected either directly on the wide bore separation tube or post the separation tube. The direct on-tube detection may require the removal of the non-transparent coatings on the outer surfaces of the cooling capillaries unless transparent coating is used for these capillaries. Depending on the material used for the separation tube, the coating, if any, on the outside of the separation tube may need to be removed as well for detection purpose. Alternatively, a transparent separation tube should be used for direct detection purpose. If the detection is in the UV range, UV transmittable materials, such as quartz, should be used. Similar transmittance requirement applies to the interior capillaries as well. For post-column detections, it may be necessary to perform some special treatment at the outlet end of the separation tube. For electrochemical detection, it is necessary to separate the electrophoresis current from the detection current. For MS detection, it may be necessary to adjust the potential at the outlet end to meet the requirement for electrospray.

The following is a description of 1) the basic theory of electrophoresis, 2) the history of the development of electrophoresis systems, 3) principles and advantages of the electrophoresis system provided by the present invention, 4) detailed description of various embodiments of the inventive electrophoresis systems, and 5) applications of the inventive systems.

1. Basic Theory of Electrophoresis

In general, there are two different kinds of movements in an electrophoresis system. The first one is an electro-osmotic flow (EOF), which is the bulk movement of the buffer solution from one (inlet) to the other (outlet) buffer reservoir at the two ends of the electrophoresis system. This movement is due to the shearing movement of a diffuse layer of cations, under the influence of the applied potential, past a more firmly held, dense layer, interacting with integral, anionic groups on the internal wall of the capillary. EOF is usually a function of the electrical field strength, buffer dielectric constant, zeta potential, and the buffer viscosity. Zeta potential is the electrical potential existing between diffuse and compact cationic layers. The buffer viscosity is dependent on bulk properties and the temperature of the buffer. Usually, EOF is the dominant movement in an open zone electrophoresis, such as capillary zone electrophoresis (CZE). However, EOF is significantly less in gel filled systems, such as slab gel or capillary gel electrophoresis (CGE), because the gel severely restrained the bulk movement of the buffer.

For charged particles residing in an electrical field, there is a second movement, in addition to EOF, called electrophoretic movement. In an electrical field, positively charged molecules (cations) migrate towards the cathode while negatively charged molecules (anions) move towards the anode. Factors controlling solute electrophoretic velocity include molecular charge, electrical field strength, viscosity of the migration media, and solute molecular geometry, etc. Neutral or uncharged molecules are not affected by the electrophoretic field and thus do not have electrophoretic mobility. Therefore, neutral or uncharged molecules can't be separated from each other in CZE. However, their separation is still feasible if a properly selected additional media is added into the electrophoresis system to bring in additional interaction mechanism, such as hydrophobic interaction and/or size discrimination. For example, if hydrophobic moiety is added to the system, a "stationary" phase is formed for different compounds to petition between the aqueous and the "stationary" phases. This hydrophobic moiety can be created either by packing the capillary with small hydrophobic particles, such as in capillary electrochromatography (CEC), or by just adding some surfactants into the running buffer, such as in micellar electrokinetic chromatography (MEKC).

In the presence of hydrophobic interaction, solutes with different hydrophobic characteristics can still be separated; even they have the same electrophoretic mobility. Therefore, it is feasible to separate these compounds in electrophoresis solely based on the differences of their interactions with the packing materials (in CEC) or with the pseduo-stationary phase formed by various surfactants, such as sodium dodecyl sulfate (SDS). Therefore, both CEC and MEKC are suited for the separation of various neutral compounds by electrophoresis.

The separation of DNA molecules by gel electrophoresis (either slab gel or capillary gel) is based on size discrimination. The gel provides a sieving mechanism to separate the DNA molecules based on their sizes. By using gel, it is possible to separate various DNA molecules even though they have the same charge-to-mass ratio.

The basic theory of electrophoresis points out that higher voltage can deliver higher separation efficiency and shorter analysis time, both are desirable for most separation tasks. Therefore, as high a voltage as possible should be applied to the buffer systems for most electrophoretic separations. Unfortunately, high electrical field generates severe Joule heat problem. Joule heat will raise the temperature of the buffer and cause many problems, such as increased diffusional spreading and Taylor dispersion (see A. Guttman el al., J. Chromatogr., 559 (1991) 285–294; S. L. Petersen el al., Anal. Chem., 64 (1992) 1676–1681; J. H. Knox, Chromalographia, 26 (1988) 329–337). At the extreme, the Joule heat can bring the buffer to boiling, putting an end to the electrophoresis process (i.e. no current). Even at temperatures below boiling, elevated temperature will change buffer viscosity, which affects both EOF and the electrophoretic mobility of the solutes. Both electrophoretic and electro-osmotic velocities are inversely proportional to buffer viscosity, thus affecting the net migration velocity for all solutes. At least, Joule heat will result in poor reproducibility. In addition, some biological samples, especially proteins, are themselves sensitive to heat, and undergo irreversible changes at high temperatures. For such reasons, most electrophoreses are usually performed in relatively low ionic strength buffers or at moderate voltages, or both. Only a few hundred to a few kV can be applied for slab gel electrophoresis because of the excessive Joule heat generated in the process. By shrinking the whole electrophoresis system to capillaries with small ID (<100 $\mu$m), it is possible to increase the electric field to more than 100 V/cm.

Heat dissipation from a capillary can be efficient if we can reduce the ID of the capillaries to extremely small (<10 $\mu$m). Unfortunately, for detection purpose, we can't use too small capillaries. The most common internal diameters of capillaries in modern CE are 50 and 75 $\mu$m. The heat dispassion in these capillaries is not perfectly satisfactory. In typical buffers, temperature elevation in these capillaries is readily observable at normal (100–350 V/cm) operating electric fields (see K. D. Davis el al., Anal. Chem., 65 (1993) 293–298; K. L. Liu et al., Anal. Chem., 66 (1994) 3744–3750). Therefore, continued efforts have been made to develop more efficient heat dissipation methods for CE systems even when small capillaries are used.

2. History of the Development of Electrophoresis Systems

The history of the electrophoresis development is full of stories how scientists battle Joule heat. For many years, the electrical field strength implemented in slab gel electrophoresis could not go beyond 100 voltages per centimeter due to the difficulty in removing the Joule heat. By extending electrophoresis into capillaries, it was possible to conduct electrophoresis at hundreds or even thousand of voltages per centimeter. High electric field can be applied to capillaries because capillaries, as compared to traditional slab gel, have a much larger surface-to-volume ratio and thus a much higher efficiency in dispassion of Joule heat. In general, the larger the surface area, the more heat it can dissipate heat. Therefore, a larger surface-to-volume ratio indicates a better heat dispassion system. On the other hand, the larger the volume, the more Joule heat it generates. To maintain a relatively high surface-to-volume ratio, it is necessary to reduce the volume. However, too small a volume imposes several challenges. First, the detection sensitivity is relatively low due to the extremely small volume in capillaries. Second, the materials commonly separated in capillaries are not enough for subsequent assays by other techniques, such as MS. Therefore, electrophoresis in capillaries by far is primarily limited an analytical rather than a preparative technique.

In addition to the surface-to-volume ratio, the heat dissipation is also related to the distance between where the heat is generated to where the surface is located for the heat to be released. The longer this distance is, the more time it takes for the heat to transport before its dissipation. For large tubes, the Joule heat generated in the middle of the tube needs to be transferred to the surface before it can be dissipated. When the size of the tube reached certain sizes, the heat generated in the middle can't be removed in time and will accumulate to increase the temperature inside. Therefore, a temperature gradient will be formed if the Joule heat can't be totally removed during the electrophoresis process. Usually, the outer surface of the system has contact with the outside, which is at a lower temperature. Thus, the temperature is lower at the outer surface and higher at the interior. When the capillary ID of the separation tube is relatively small (e.g. <100 $\mu$m), the internal capillary can be treated as a single point when we consider the Joule heat distribution (see J. H. Knox, Chromatographia, 26 (1988) 329–337). However, when the diameter is significantly larger, a temperature gradient will be formed inside the separation tube with the center of the separation tube at the highest temperature. Heat generated near the surface can be readily released to the outside through the surface while it takes longer time for the heat generated in the middle of the separation tube to reach the outer surfaces. The following calculations demonstrate the importance of the tube size for heat dissipation.

In theory, the heat generated per unit volume (Q) in an electrolyte is given by $Q=E^2 \lambda c \epsilon$, where $\lambda$ is the molar conductivity of the solution, c is the concentration and $\epsilon$ the total porosity of the medium, i.e. $\epsilon=1$ for open tube and $\epsilon=0.4$–$0.8$ for packed tube. With typical values, E=50,000 V/m, $\lambda=0.015$ m$^2$/mol*$\Omega$, C=10 mol,m$^3$, $\epsilon=0.8$, we obtain $Q=300\times10^6$ W/m$^3$=300 W/cm$^3$.

In the case of a tube, the temperature excess, $\theta_{core}$, within the core region (i.e. the difference between the temperature on the axis of the tube and at its inner wall) is given by $\theta_{core}=Qd_c^2/16\kappa=(E^2\lambda c\epsilon)(d_c^2/16\kappa)$. For $d_c=100$ $\mu$m and $\kappa=0.4$ W/mK, $\theta_{core}=0.47$. However, for $d_c=500$ $\mu$m and $\kappa=0.4$ W/mK, $\theta_{core}=12$, which is really excessive.

The temperature excess across the wall, $\theta_{wall}$, is given by $\theta_{wall}=(Qd_c^2/8\kappa_w) \ln(d_0/d_c)$, where $d_0$ is the OD of the tube and $\kappa_w$ is the thermal conductivity of the tube wall material. Again, using typical values of small capillary, $d_0/d_c=2.0$ and $\kappa_w=1.0$ W/mK, we obtain $\theta_{wall}=0.1$ 1 K. Thus, both $\theta^{core}$ and $\theta_{wall}$ are small for regular capillaries. The above calculations demonstrate two points. First, the temperature excess, $\theta_{core}$, is proportional to the square of the ID of the tube. Second, $\theta_{wall}$ is negligible for large tubes, where $d_0/d_c$ close to 1.0.

Therefore, the focus in a large tube should be on the $\theta^{core}$.

In addition to physically reducing the size of the separation channel to avoid the Joule heat, continues efforts have been made to find better ways to remove the excessive Joule heat associated with electrophoresis process. Before capillaries were available for electrophoresis, the electrophoresis unit has to be submerged in a big water bath to dissipate the Joule heat (see R. Virtanen, Acta Polytech Scand 123 (1974) 1–67). Even for capillaries, various methods, ranging from forced air convection flow, liquid coolant to solid contact to cool the capillaries, have been applied to CE to control the capillary temperature. Some of these methods have been incorporated in commercial instrumentation already. For example, Weinberger et al. (in U.S. Pat. No. 5,021,646, hereby incorporated by reference) describes a CE unit utilizing an air-cooled cartridge. A Peltier heat sink is employed to cool the air around the capillary. The temperature of the capillary is determined by measuring its electrical resistance. When the temperature of the capillary requires adjustment, a fan drives the cooled air across the capillary in the cartridge. Similarly, Christianson (in U.S. Pat. No. 5,122,253, hereby incorporated by reference) describes the use of a stream of pressurized gas in a transverse flow through a capillary region. A rotary fan creates a gas flow, which is axial to the helix formed by the capillary tube, to cool the capillary.

In addition to air-cooling systems, several methods of using liquid cooling have also been developed. Burolla et al. (in U.S. Pat. No. 5,198,091, hereby incorporated by reference) explains a liquid cooling apparatus. The cooled capillary cartridge is bisectional and contains an inner chamber. The inner chamber holds the capillary and can also contain a circulating liquid coolant. The coolant is described as either water or, preferably, a completely fluorinated hydrocarbon. Dill et al. (in U.S. Pat. No. 5,164,064, hereby incorporated by reference) reports an improved liquid cooled device, which includes a capillary cartridge with a coolant flow channel with little or no dead volume to improve uniform cooling.

Refrigeration has also been incorporated into the liquid cooling system for CE. For example, Penaluna et al. (in U.S. Pat. No. 5,183,101, hereby incorporated by reference) described the use of a refrigeration device to cool the coolant circulation around the capillary. The refrigeration device is comprised of a heat exchanger, a compressor and a capillary nebulizer. The refrigeration device is electrically insulated from the buffer solution and non-conductive coolant, such as fluorochemicals, was used to prevent any electrical contact between the refrigeration device and the electrophoresis buffer. The buffer solution is cooled down when passing through the refrigeration coils. Several groups (see B. L. Karger, A. Paulus, A. S. Cohen, R. J. Nelson, U.S. Pat. No. 4,898,658; B. L. Karger and R. J. Nelson, U.S. Pat. No. 5,085,757; M. D. Morris and T. L. Rapp, U.S. Pat. No. 6,103,081, hereby incorporated by references; R. J. Nelson et al., J. Chromatgr., 480 (1989) 111–127) have attempted to control the capillary temperature by allowing capillaries in direct contact with a Peltier heat sink. The Joule heat generated in the capillary is directly passed onto the heat sink through physical contact.

All of the aforementioned approaches are specific means of cooling the capillary from the outside of the separation capillary and thus have significant shortcomings. For example, forced air-cooling alone is limited in its capacity to remove heat from the capillary column. It is not very efficient even for capillaries as large as 50 $\mu$m. Liquid cooling from the outside of the capillary can be effective when the capillary ID is small (<75 $\mu$m). However, it is less effective when the capillary ID is relatively large (>75 $\mu$m). The direct attachment of capillary to a heat sink suffers the same problem as liquid cooling when the capillary ID is significantly increased. In addition, the direct contact of capillary with an electric conductive material, such as aluminum, would change the uniformity of electrical field inside the capillary. Therefore, none of the existing methods can efficiently cool CE system enough to completely remove the Joule heat generated from the electrophoresis process. Joule heat problem becomes more severe when the ID of the capillary increases.

The lack of an efficient way of removing Joule heat from the electrophoresis systems limits the usefulness of electrophoresis as a whole. A new means of cooling the capillary as well as other electrophoresis system in an efficient manner is needed in order to expand the usefulness of electrophoresis, especially for large-scale applications. Tornopolsky described a different approach to cool large preparative electrophoresis system in U.S. Pat. No. 5,104,505 (hereby incorporated by reference). Tarnopolsky chose to cool the preparative FFE system from inside the separation chamber with fibers assembled together with some porous spacers. That approach seems to be effective in improving the cooling efficiency for relatively large electrophoresis systems. However, it is not practical to use that design for smaller analytical scale system. This invention describes the details of making high performance electrophoresis system using wide bore separation tube with significantly improved Joule heat control.

3. Principle and Advantages of the Electrophoresis System of the Present Invention Since one of the objectives of the present invention is to increase the amount of samples loaded onto the separation system, we need to deal with much larger electrophoresis channels. The current invention takes advantages of this fact of using larger channels by inserting smaller capillaries, called cooling capillaries (or cooling capillary lines), into the center of the electrophoresis channels. If the channels are sufficiently large, it may be possible to add some rods and/or open tubes into the separation tube to combine with the cooling capillaries to form the structure necessary for the designed system. These cooling capillaries form a loose capillary bundle inside the electrophoresis system. The interstices between the inner surface of the channels and the cooling capillaries form the separation space. Samples are introduced into the interstices and are separated during the electrophoresis process. A proper coolant is forced through the cooling capillaries to carry away the excessive heat generated in the electrophoresis process. A detector either on-line or off-line is used for monitoring the separation process.

There are numerous advantages associated with the present invention. One application of this invention is in high performance microbore electrophoresis (HPME), which offers many advantages over the current CE and slab gel electrophoresis systems.

First, an important advantage that this invention offers is an unprecedented high efficiency in removing the Joule heat associated with the electrophoresis process. This high efficiency in heat removing is achieved due to the combination of several factors. The most important one reason for this high efficiency is the significant increases in cold surfaces. By inserting capillaries with a high surface-to-volume (S/V) ratio into the separation chamber the S/V of the whole separation system can be significantly increased. The second reason is that the individual capillaries of the cooling capillary bundle are distributed inside the separation tube and break the permissible interstices in the separation tube into multiple smaller spaces. These capillaries are small enough that they virtually divide the interstices within the separation tube into many tiny smaller spaces and, at the same time, introduces the cold surfaces immediately next tot these tiny spaces to remove the heat. Since the OD of the cooling capillaries are sufficiently small, usually a few hundred micrometers and occasionally larger, these smaller spaces virtually form multiple capillary like micro-channels. By carrying the heat away from its origin, this invention eliminates the need for heat to transport to the outer surface. Thus, it significantly shortens the distance between the heat generation and the cooling reservoir as the coolant has been brought to the interior part of the electrophoresis system. The third reason is that the quick removal of heat from its origin reduces the chances for heat to accumulate over the time in the system.

Second, depending on the objective of specific applications, this invention offers the flexibility of achieving different degrees of cooling by varying the combination of a variety of the number and sizes of the cooling capillaries and the rate of coolant passing through the capillaries. For example, since the temperature of the coolant is controllable, it is possible to increase the temperature gradient between the heat source and the coolant by lowering the coolant temperature. Thus, the cooling efficiency can be significantly increased.

Third, another advantage is that this new electrophoresis system is compatible with existing HPLC autosamplers and detectors and thus suitable for full automation.

Fourth, this invention can be applied to a broad range of electrophoresis formats, including capillary, slab gel, lab chips, and continuous 2-D electrophoresis. For example, the ID of the separation tube in HPME could be 1 mm or even larger. The OD of the cooling capillaries can be quite different providing the whole bundle can be inserted into the separation tube and the various parameters meet the restrictive relationships. Similarly, lab chips based electrophoresis system can be made in a similar way. The slab gel and the continuous 2-D electrophoresis devices can also be made by incorporating the cooling capillaries into the system. In general, these systems are more flexible in terms of dimensions and sizes.

Fifth, the interstices between the outer surfaces of the cooling capillaries and the inner surface of the separation tube allow buffer and samples to pass through. Since the cooling capillaries are loosely bounded but not glued together, buffer and samples can move from one channel to the other while passing through the capillary. Therefore, analytes with the same mobility will move in the same speed inside the capillary and come out simultaneously. Since the current invention allows solutes to freely move inside a single chamber, the same solutes experience similar conditions during the electrophoresis process and thus will migrate at a similar speed. Thus, it is possible to inject a larger amount of samples into the system and expect the samples will come out at the same time. This is quite different from the separation inside the individual capillaries of the capillary bundle described previously (N. A. Guzman L. Hernandez, and B. G. Hoebel, Biopharm. 2 (1989) 2–37), where the analytes are segregated from each other and them may not come out the capillaries at the same time even they are injected at the same time and run under the same conditions. The inconsistence among the capillaries is due to the fact that it is hard to have all the capillary surfaces to be the same. Therefore, it is hard to achieve the same migration time of the same analytes from different capillaries, which makes the detection as well as the collection of the fractions difficult.

In addition, since the number of cooling capillaries can be increased as many as the separation tube size allows, this inside capillary bundle is very efficient in removing Joule heat. Therefore, it is possible to make a very large-scale preparative electrophoresis system including a large tube, parallel array tubes, a slab gel (even slab none-gel), and/or continuous 2-D electrophoresis without worrying about Joule heat.

Sixth, the fact that the separations happen in the interstices formed between the inner surface of a relatively large separation tube and the outer surface of smaller capillaries allows us to develop various surface chemistries on the surfaces of the capillaries to meet different needs. For example, we may remove the polyimide coating on the outside of the fused silica capillaries and expose the uniform silica surface, which will have the same chemical properties as the inner surface of the separation tube. Therefore, the EOF in the interstices will have a flat front profile. In addition, this silica surface can be further treated with various agents to modify the surface to be either neutral (good for reducing protein adsorption problems) or charged for different purposes.

4. Specific Embodiments of the Present Invention

Figure 8:
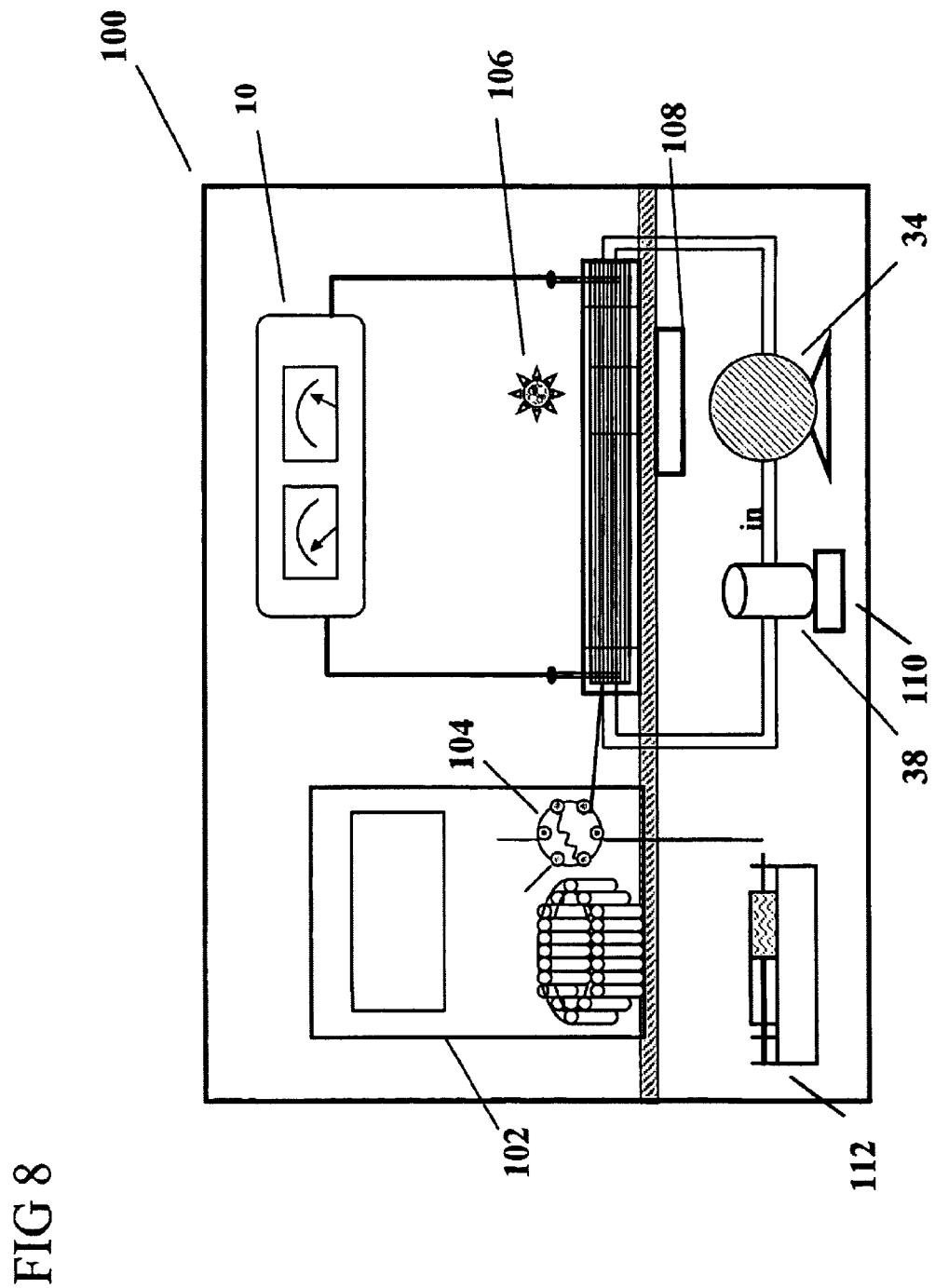
FIG. 8 is a general view of the high performance wide bore electrophoresis instrument incorporated with the separation cartridge, the cooling system, the high voltage power system, the sampling system, and the detection system.

In general, this invention discloses a completely new electrophoresis system 100, which has mainly a power supply 10, a separation cartridge 20, a cooling unit 110, a sampling device 102 and a detector 28 as illustrated in FIGS. 1 and 8. The power supply 10 provides a high voltage power for the electrophoresis process in the separation cartridge 20.

I. Single Separation Tube System

The separation cartridge 20 usually has one or more separation tubes 12 (or slab, or chip or continues 2-D, etc) with an internal dimension of larger than 10 micrometers and contains an electrolytic buffer solution 14, which is in fluidic communication with the buffer solutions 14 in the first buffer reservoir 6 and the second buffer reservoir 16 at the inlet end 8 and the outlet end 18 of the separation tube 12, respectively, for performing electrophoresis.

The electrophoresis system 100 also contains a high voltage power supply 10, which drives the buffer solution 14 along with samples inside the separation tube 12 to move from a first buffer reservoir 16 to a second buffer reservoir 16. Buffer 14 enters the separation tube 12 through the inlet end 8, passes through the separation tube 12, and exists out of the separation tube 12 through the outlet end 18 to accomplish the fluidic path in the system. The electrical path starts from the power supply 10, through conductive electrical wire 22 to reach an electrode 24, which is usually a platinum wire placed in buffer solution 14. Then, the electrical current passes through the electrolytic buffer solution 14 within the separation tube 12 and reaches the other electrode 24 placed in the other buffer reservoir 16 at the other end of the separation tube 12. The electrode 24 is connected to another electrical wire 22, which is connected to the other outlet of the power supply 10.

The electrophoresis system 100 also has an injection device 102 (FIG. 8) for introducing samples into the separation tube 12 through a sample line 26, which is placed either inside or near the inlet end 8 of the separation tube 12.

The electrophoresis system 100 also has an online detector 28 to detect samples separated by the separation tube 12. Alternatively, the separated samples can also be detected by mounting a detector 28 on a detection line 30, which is inserted inside or near the outlet end 18 of the separation tube 12. Detection line 30 is located at the opposite end of the sampling line 26 and can also serve the purpose of transporting the separated samples directly into detectors like MS and/or NMR.

The electrophoresis system 100 also includes a cooling system, which contains at least an interior heat sink and preferably plus an exterior cooling compartment 32. The exterior cooling compartment 32 can be any cooling system employed in modern CE instruments and preferably a liquid cooling system. The interior heat sink is inside the separation cartridge 20 and consists of a bundle of cooling capillaries 40, which passes through the separation tube 12 to provide added cooling to the exterior cooling 32. A driving device 34, such as a pump or a compressor, forces coolant 36 from coolant reservoir 38 to pass through the cooling transferring lines 42, which is connected to the cooling capillaries 40 through a connector 48 (FIG. 2). After passing through the cooling capillaries 40, the coolant 36 returns to the reservoir 38 through coolant transferring lines 42.

A. Separation Cartridge

The separation cartridge 20 includes separation tube 12, a plurality of cooling capillaries 40, one or more buffer reservoirs 16, and exterior cooling 32. While the present invention is not limited to the specific means of making the device, there are at least two different ways of making the separation cartridge 20. One is to assemble the components together to form the cartridge as shown in FIG. 2. The other is to fabricate the separation cartridge 20 by integrating all of the components in a specific position within a pre-designed housing as shown in FIG. 6.

a) Separation Tube

Figure 3A:
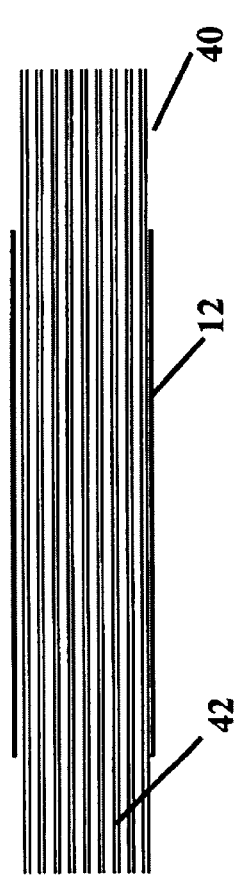
FIG. 3 is detailed views of the intersections of the cooling capillaries system from the front (A and B) and the side (C and D). The cooling capillaries may have either the same (A) or different (B) diameters. The cooling capillaries can be incorporated into either a separation tube (C) or a flat chamber (D) system.
Figure 3B:
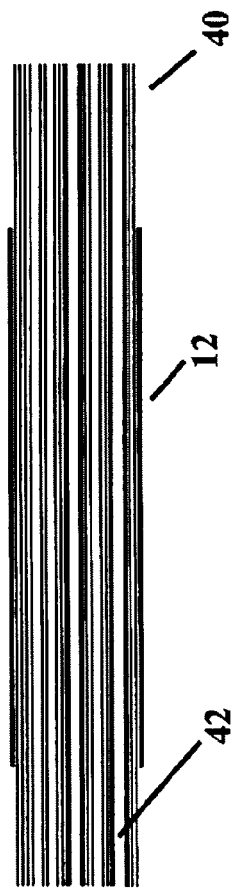
Figure 3C:
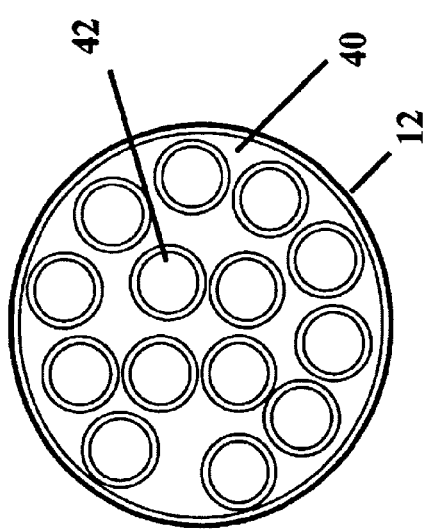
Figure 3D:
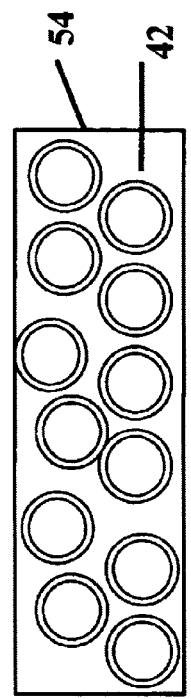

In one embodiment, the separation cartridge 20 comprises an electrically non-conductive separation tube, one or more electrically non-conductive cooling capillaries 40 dimensioned to substantially small to pass through the said separation tube 12, the cooling capillaries 40 being longer or shorter but preferably longer than the separation tube 12 with the additional length for connecting to other parts of the system. If the cooling capillaries 40 are shorter than the separation tube 12, adaptors have to be used. FIGS. 3A and 3B are the detail views from the front showing the cooling capillaries 40 inserted inside the separation tube 12 with the individual capillaries 42 having the same (FIG. 3A) and different (FIG. 3B) IDs and ODs. FIG. 3C is the side view showing the cross section of the cooling capillaries 40 inserted inside a separation tube 12. FIG. 3D is the side view showing the cross section of the cooling capillaries 40 between two plates 54.

Optionally, some solid rods and/or open tubes or both dimensioned to substantially small to pass the separation tube 12 can also be combined with the cooling capillaries. For simplicity, these solid rods and/or tubes are included as part of the coaling capillaries 40 in this discussion.

A variety of electrically insulative material can be used for the separation tube and the cooling capillaries in the present invention, including, but not limited to, glass, quartz, fused silica, ceramic, and polymers such as Teflon®, polycarbonate, polymethylmethacrylate (PMMA) or silicone. For the consideration of heat dispassion and optical transparency, fused silica is often the preferred material.

While the present invention is not limited to the specific shape (such as circle, square, rectangular, etc) and size of the separation tube 12 and the cooling capillaries 40, in one embodiment, the said separation tube 12 has an inner surface and the said cooling capillaries 42 have outer surfaces. Those surfaces provide the driving forces in electrophoresis.

For the purpose of various separations, the interior of the said separation tube 12 and the exterior of the said cooling capillaries 40 can be coated with any number of insulative materials, including, but not limited to a polymer (e.g., polyacrylamide and polyvinyl alcohol). For example, the same coating materials can be applied to both surfaces to create a flat front in the electro-osmotic flow profile. While the present invention is not limited to specific design and embodiments, in one embodiment, each of the compartment for the separation cartridge 20 can be assembled together. FIG. 2 is the front view of a separation cartridge 20 containing a separation tube 12. Cooling capillaries 40, which comprised of multiple individual capillaries 42, are inserted into the separation tube 12. The two opening ends 8 and 18 of the separation tube 12 are in fluidic communication with the buffer 14 in the buffer reservoirs 6 and 16, which can be made of plastic "T"s 44. High potential is applied to the separation tube 12 through electrode 24, which are placed in the buffer reservoir 6. A coolant connector 48 is attached to one end of the cooling capillaries 40. The connections between the separation tube 12 and the "T" 44 and between the cooling capillaries 40 and the coolant connector 48 are properly sealed with suitable union and ferrules. Between the separation tube 12 and the T 44 (or cross 46), PEEK screws 50 along with a suitable ferrule 52 can be used to prevent the leakage of buffer 14 out of the separation fluidic path. In addition, part of the separation tube 12 is submerged into an exterior cooling chamber 32, which allows coolant pass through to cool the separation tube 12 externally.

Figure 6A:
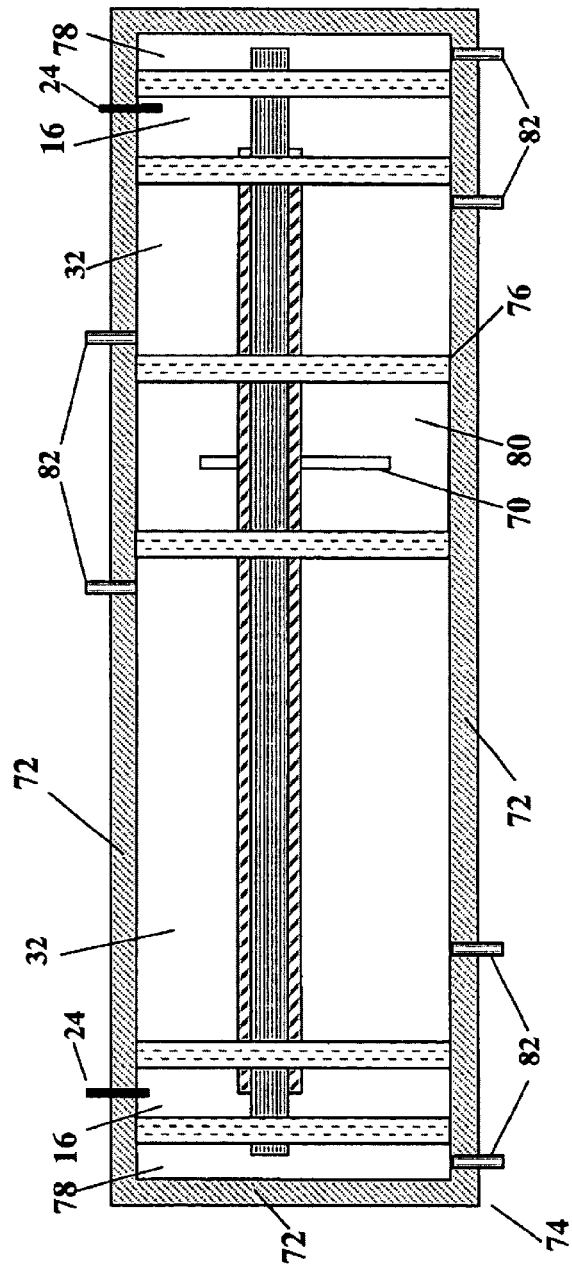
FIG. 6 shows the top (FIG. 6A) and the front (FIG. 6B) views of an integrated separation cartridge.
Figure 6B:
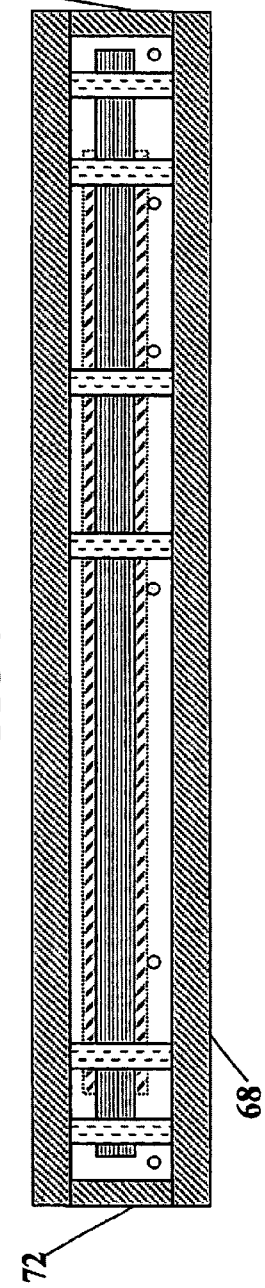

In yet another embodiment, the separation cartridge 20 is made with all components integrated together in a solid housing 74 (FIG. 6). FIG. 6A and 6B are the top and front side views of an integrated separation cartridge 20, respectively. The integrated separation cartridge 20 has a rectangular flat base 68, which has a small hole (or slit) at a pre-determined location for detection window 70. On top of the base 68, four pieces of side panel 72 are glued to the rectangular flat base 68 to form a housing 74 with only the top open. Within the housing 74, there are several dividing boards 76, which separate the housing 74 into multiple compartments (FIG. 6A). From outer side to inside, the two at the ends are coolant compartments 78. The immediately adjacent two are buffer reservoirs 6 and 16, which follow by two exterior cooling compartments 32. The last one is the detection compartment 80, which has the detection window 70 and is totally separated from the coolants 36 in the exterior cooling compartments 32. There is a small hole (not shown) on each of the two side panels 72 at the two ends of the housing 74 and all of the dividing board 76 within the housing 74. All of these holes are aligned in a straight line to allow the separation tube 12 along with the cooling capillaries 40 to be inserted. The two ends 8 and 18 of the separation tube 12 are terminated within the buffer reservoirs 6 and 16 to keep the fluidic communication with the buffer solution 14. The cooling capillaries 40 passes through the separation tube 12 with both ends in the coolant compartments 78. After the separation tube 12 and the cooling capillaries 40 pass the small holes on the dividing boards 76, the remaining voids between the separation tube 12 and the holes are sealed with suitable glue. There are some coolant inlets and outlets 82 on the coolant compartment 78 and the exterior cooling compartment 32, both of which may be covered with a cover plate to make a completely sealed system for coolant 36 to pass through. The cover plate (not shown) can cover the whole top of the housing 74 as long as it has hopes for the detection window 70 and the buffer reservoir 16. Alternatively, the reservoir shown in FIG. 4D can be added on top of this housing 74 in the buffer compartments to make the buffer and reagent changing process fully automatic. High potential is applied to the separation tube 12 through electrode 24, which are placed in the buffer reservoir 6.

b) Reservoirs

Figure 4C:
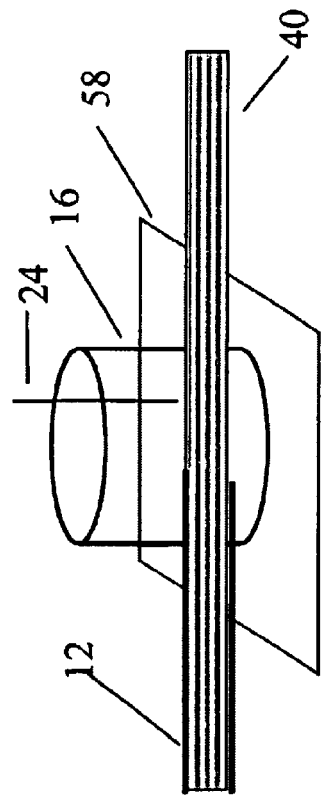
FIG. 4 shows some alternatives to the T-shaped reservoir: A) a cross, B) an open reservoir, C) an open reservoir mounted on a fixed surface, and D) a closed reservoir with a tube and a switch to communicate with outside.
Figure 4D:
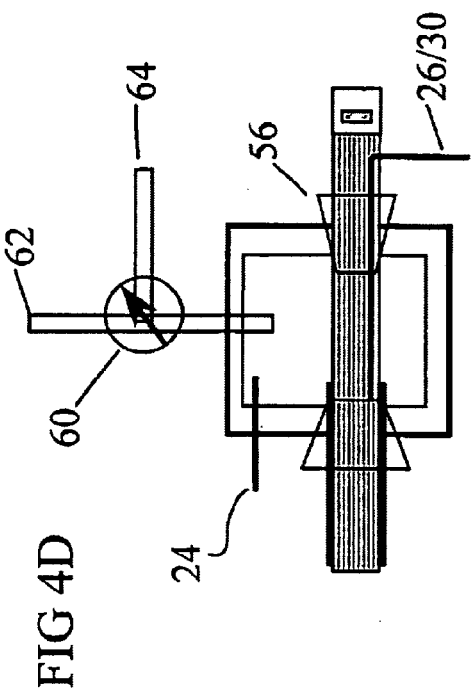
Figure 4A:
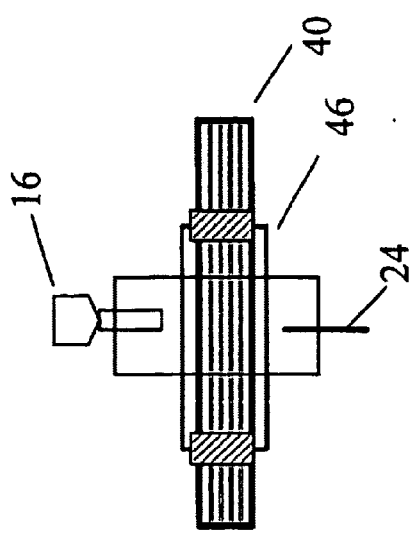

The separation cartridge 20 has at least one and often two buffer reservoirs 6 and 16 at the ends 8 and 18 of the separation tube 12, respectively (FIGS. 1, 2 and 8). The reservoirs can be, but not limited to, T-shaped 44 (FIG. 2) or cross-shaped unions 46 (FIG. 4A), which can be obtained from commercial sources like Upchurch. These unions have three (for T) or four (for cross) openings for connecting with other parts. In the middle of the T 44 or cross 46 unions, there is a hole, which can be, but not have to be, slightly smaller than the OD of the separation tube 12 but larger than the cooling capillaries 40. The cooling capillaries 40 pass through this hole and extended out of the opposite openings of the T (or the cross) (FIG. 4A). The remaining opening of the T (or one of the two remaining openings of the cross) is connected to a buffer reservoir 16. Metal (platinum wire preferred) electrode 24 can be placed either in the reservoirs 6 and 16 (for the T, FIG. 2) or in the additional inlet of the cross 46 (FIG. 4A). In the later case, the electric communication between the electrodes 4 and 24 and the buffer solution 14 can be established directly or through a semi-permeable membrane. The connections to all of the openings on the unions (44 and/or 46) except the ones towards the buffer reservoirs 6 and 16 should be properly sealed to prevent the leakage of the buffer 14. While the specific dimensions do not limit the application of the invention, in one embodiment, a regular 1/16" ID plastic fitting is sufficient to seal the opening between the union (44 and/or 46) and the separation tube 12 that has an OD of 1.5 mm. The opposite side of the T 44 or cross 46 can be sealed either by gluing the cooling capillaries 40 to a plastic tubing and then seal the end through a regular fitting. A proper fitting with a suited sleeve can seal the third opening on the cross.

Figure 4B:
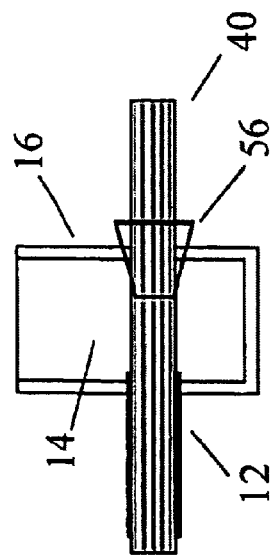

In addition to the "T" 44 and "cross" 46, the buffer reservoir 6 or 16 can be designed differently. FIG. 4B is an open container buffer reservoir 16. The separation tube 12 came into contact with the buffer solution 14 from one end while a stopper 56 is used to block the leakage of buffer 14 and allow cooling capillaries 40 to pass through. The interstices among the cooling capillaries 40 are sealed with proper glue. FIG. 4C is an open reservoir mounted on a flat surface 58. The contact between the cooling capillaries 40 and the surface 58 can be sealed with proper glue. FIG. 4D is a closed reservoir 16, which is linked to a three-way switch 60. When the system is in the electrophoresis mode, the switch 60 is open to air 62 to keep the same pressure on top of the buffer 14 for both sides. If it is necessary to flush the separation tube 12 or to fill new buffer 14 into the buffer reservoir 16, the switch 60 is connected to the reagent position 64. An inducing capillary 26 (or 30) can be added to this reservoir to introduce additional communication between the separation system and the outside devices. This feature offers the potential for automating the process. In addition to the function of sample injection (26) and post-separation detection (30), this capillary can also be used for reagent/buffer addition as well.

Further, FIG. 5 shows some more alternative reservoirs 16, which allow the separation tube 12 to be in either horizontal or vertical or both positions. The vertical position requires the separation tube 12 to be made of soft materials such as plastic tubing. FIG. 5A is an open U-shape reservoir 16, which has an opening 66 at the end of the top for exposing to the atmosphere pressure and an electrode 24 for electric contact with the high voltage power supply 10. The uniqueness of this reservoir is that it allows the cooling capillaries 40 to reach the buffer solution 14 vertically. This feature may be desirable for some systems. FIG. 5B is a closed U-shaped reservoir 16, which has an opening 66 for connecting to other devices. If it is connected to a switch 60 as shown in FIG. 4D, this closed U-shaped reservoir will function the same as the FIG. 4D reservoir. FIG. 5C is an L-shaped reservoir 16 with the opening 66 at the short end of the L. FIG. 5C is fundamentally the same as FIG. 5B except the location of the opening 66, which is more close to the end of the separation tube 12.

Alternatively, the two ends 8 and 18 of the separation tube 12 can be in direct contact with two reservoirs 6 and 16, respectively, without the T 44 or cross union 26 as shown in FIG. 6. The reservoirs can be totally independent of each other or, preferably, are fabricated on a single block to maintain mechanical stability. In one embodiment, the said reservoirs can be made as a whole part of the said separation cartridge. By fabricating the reservoirs on a single cartridge, it is easier to control the level of the buffer as the two reservoirs have the same base. In this case, the said separation tube is placed in the middle of the cartridge and the ends of the tube are in fluid communication with the buffers in the said reservoirs. Usually, the tops of the reservoirs are open to the air for placing electrodes and for replacing buffers. However, the top can be sealed when either pressure or vacuum is applied to them to move the liquid inside.

B. The Cooling System

The cooling system may consist of six components: a coolant 36, a cooling unit 110 to cool the coolant 36, a pump 34 to drive the coolant 36, cooling capillaries 40, coolant connector 48 for interior cooling, and chamber for outside cooling 32 (FIGS. 1 and 2). Some parts of this cooling system are built as an integral part of the separation cartridge 20 (FIG. 6).

The coolant 36 in the present invention could be gas, liquid or solid materials, including, but not limited to, air, nitrogen gas, ammonia, carbon dioxide, water, fluorochemicals, liquid nitrogen, ice, and dry ice, etc. A non-conductive and recyclable material, such as fluorochemical, would be preferred.

In one embodiment, there is a cooling unit 110 to cool the coolant 36. The cooling unit 110 can be a Pilter cooler or an exterior chiller. There is also a high-pressure pump 34, which drives the coolant 36 to pass through the whole system. The pump 34 is capable of delivering relatively high pressure (>1000 psi) to force the coolant 36 to pass through the coolant lines. In order to prevent baseline noises for online detection purpose, this pump 34 should be able to deliver coolant at relatively smooth fashion to reduce pulses. Therefore, HPLC pump is best suited for this purpose.

Figure 7:
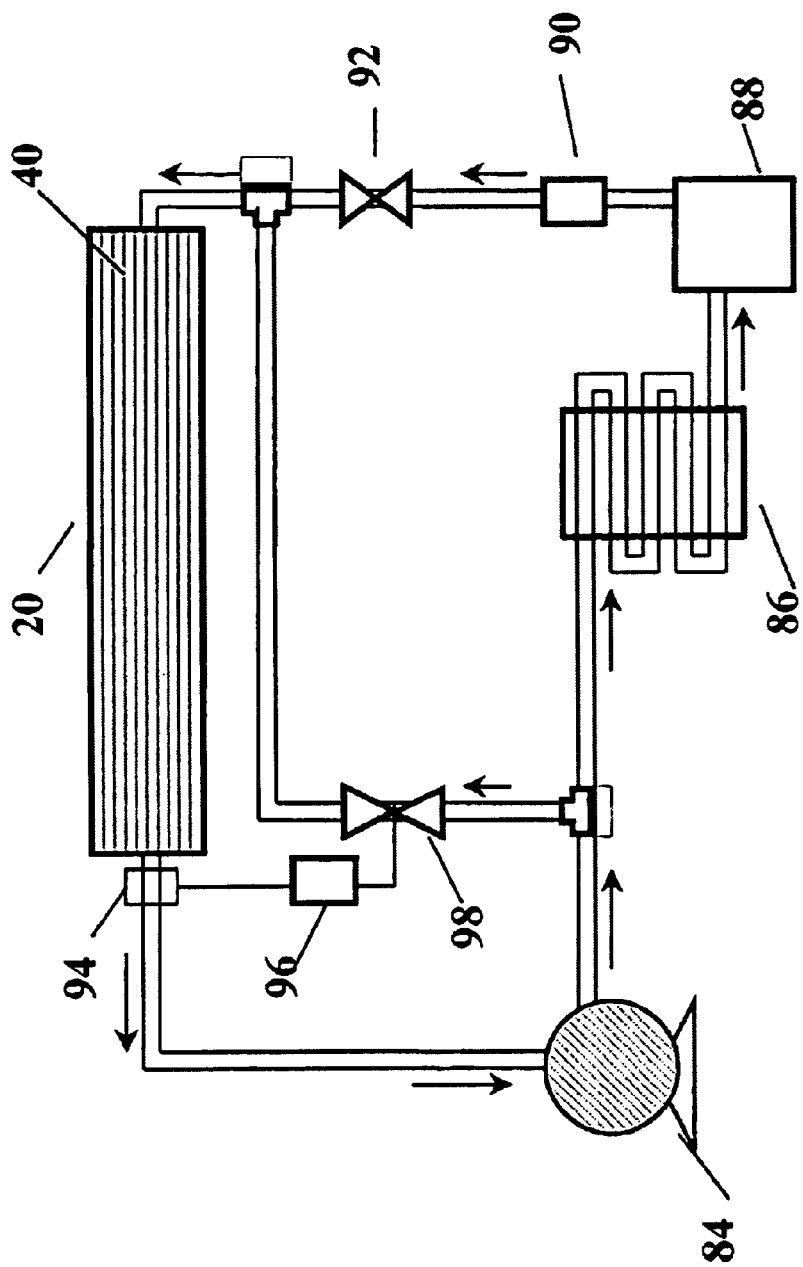
FIG. 7 shows the basic principle of an air conditioning system using the cooling capillaries as the evaporator in the air conditioning system.

Alternatively, the cooling unit 110 and the pump 34 can be replaced with an air-conditioning system as described in FIG. 7. In one embodiment, a compressor 84 can be used to pressurize the coolant 36 into liquid (or solid, e.g. ammonium) state, which evaporates into gas passes through the cooling capillaries 40 directly (FIG. 7). In this embodiment, the cooling capillaries 40 serve the purpose of an evaporator in a typical refrigeration cycle. FIG. 7 shows the basic principles of an air conditioning system with the cooling capillaries 40 serving as the evaporator. Compressor 84 pressurizes the gas phase coolant 36 (refrigerant in this case) to high temperature. The gas phase coolant 36 passes through condenser 86 and releases the heat to become pressurized liquid, which is stored in the coolant receiver 88. Under pressure, the liquid coolant 36 continues to pass the filter 90 and reaches the thermostatic expansion valve 92. Than, the liquid coolant 36 enters the cooling capillaries 40, where it absorbs heat from the outside of the cooling capillaries 40 and evaporates into gas phases upon exiting the other end of the cooling capillaries 40. This gas phase coolant 36 is recycled by the compressor 84 and enters the next refrigeration cycle. The thermostatic expansion valve 92 controls the amount of the pressurized liquid coolant 36 to vaporize in the cooling capillaries 40. In addition, a thermo-couple 94 is mounted near the exit of the cooling capillaries 40 and provides the feedback to the thermostat controller 96, which adjusts the operation of a solenoid valve 98 to provide a hot bypass to avoid over-heating of the compressor 84.

The cooling capillaries 40 can be made of various materials including but not limited to inorganic and organic polymer materials. Depending on the specific applications, the generally desired characteristics of this material for the said cooling capillaries include, but not limit to, good thermo-conductivity, low electrical conductivity, high mechanic strength, good optical properties (for only detection only), easy to chemical modification of its outer surface, and easily available in various dimensions (see Example 1 for details) including very small diameter from commercial vendors, etc. Most materials can't meet all of these criteria. It seems that fused silica capillaries can meet most of the criteria and is the best-suited material for constructing these cooling capillaries 40, which can be the same or have different dimensions.

There are two electrical insulation issues when operating the electrophoresis with the cooling means of the present invention: a) electric insulation between the coolant driving force 34 (e.g. pump or compressor) and the heat sink (cooling capillaries 40) and b) electric insulation between the heat sink and the electrophoresis buffers. To address these concerns, cooling capillaries should be non-conductive, such as commercially available capillaries. These capillaries have a non-conductive layer to enhance the insulation effect of the fused silica capillaries. A number of materials may comprise this layer, including ceramic and polymer. For example, the polyimide coating can handle as high a dielectric strength as 1575 kV/cm (see Flexible Fused Silica Capillary Tubing Standard Product List, Polymicro Technologies, Inc., Phoenix, Ariz., 1996). For the convenience of online detection, capillaries with transparent polymer coatings can be used. This insulation is critical to keep the electrophoresis power from leaking into the instrument. Such insulation may be of a variety of materials, including the polyimide coating described above. The buffer reservoirs 6 and 16 are shielded from the metal parts of the pump 34 (FIG. 1) and/or compressor 84 (FIG. 7) through the non-conductive capillaries 42 plus non-conductive coolant 36. At the worst scenario, a by-pass function of the system will eliminate the danger of current leakage.

The coolant 36 can pass through the cooling capillaries 40 from either end. For better heat transfer, however, it is often preferred that the coolant passing through the separation tube from the opposite direction of the liquid flow, i.e. counter current against the electrophoretic flow in the interstices between the cooling capillaries 40 and the separation tube 12. For most electrophoresis process, this means from the detection end 18 to the injection end 8. The coolant 36 coming out of the outlet end of the cooling capillaries 40 can be guided out to the waste or recycled.

The cooling capillaries 40 and the incoming coolant 36 are connected through connectors 48 (FIG. 2). Usually, either one or two ends 8 and 18 of the separation tube 12 are attached to the connectors 48. While two connectors 48 (both inlet connector and outlet connector) are required for recycling of the coolant 36, only one connector 48 (inlet connector) is needed if the coolant 36 is not recycled for continued use.

Usually, the inlet connector 48 is linked to the coolant at a high pressure generated by a pump 34 or a compressor 84. The connector 48 has to be mechanically strong enough to tolerant such a high pressure, which could be as high as several thousands of pound per square inch (i.e. >1000 psi). The connections between the inlet connector 48 and cooling capillaries 40 as well as the coolant line 42 has to be tight enough to tolerant such a high-pressure too. While not limited by the dimensions, the inlet connector 48, in one embodiment, can be a metal internal union (such as Valco Cat. No. ZU1T) with two male or female ends with one connecting to the coolant line 42 while the other end connected to the cooling capillaries 40.

While there are many different designs, in one embodiment, the end of the connector 48 that link to the cooling capillaries 40 has a hole to allow the cooling capillaries 40 to pass through. The said hole has a dimension slightly larger than the overall outer diameter of the cooling-line bundle. A small sleeve can be put outside of the cooling-line bundle to adapt the bundle to the connector. The sleeve also serves the purpose of protecting the cooling capillaries from broken.

A seal between the connector and the outer surfaces of the cooling capillaries 40 is created to prevent the leakage of the coolant 36 into the separation tube 12. The material used for creating such a seal can be, but not limited to, rubber, liquid sealant, and/or epoxy glue, etc. While it is not limited to one specific design, in one embodiment, the seal can be created by gluing one end of all the cooling capillaries together with, such as, but not limited to, super glue or epoxy glue. Alternatively, in one embodiment, all of the cooling capillaries 40 pass through a rubber seal, which is tightly screwed inside the connector 48.

While it is not the intent of this invention to be limited by the specific size, a $1/16''$ tubing is sufficient for cooling a single separation tube 12 with an ID smaller than 1 millimeter. For example, in one embodiment, the connector 48 to the high-pressure end can be connected to an HPLC pump 34 through a $1/16''$ (OD, ID >0.005'') tubing. When multiple separation tubes 12 are involved, the flow rate will increase and the ID and the OD need to be increased according to allow sufficient flow to pass through.

The outlet end of the cooling capillaries 40 usually does not experience high pressure. The outgoing coolant 36 can be guided back to the circulation system or disposed. When recycled, an outlet connector 48 is used to link the cooling capillaries 40 to a coolant recycle line 42 to complete the loop (FIG. 1). This outlet connector 48 could be the same as the inlet connector 48 or could be a simple plastic tube that is sealed properly with the cooling capillaries 40 to avoid fluidic leakage.

In addition to the inside cooling, one of the conventional cooling methods as described previously is applied to the outside of the separation tube 12 to cool the electrophoresis system further (FIGS. 1, 2 and 6). The coolant 36 for the outside cooling 32 can be totally separated from the coolant 36 for the interior cooling or coming from the same cooling source. If the coolant 36 is separated from the interior-cooling source, a separated pump and coolant reservoir may be needed. Another way to provide the separated external cooling is to use a liquid bath attached to a thermo-electrical cooling sink to provide the cooling.

If the outside cooling and the interior cooling come from the same source, there are two ways of sharing the same coolant, i.e. parallel or sequential. One way is to split the cold coolant out from the source into two steams in parallel with one going into the cooling capillaries 40 and the other going to the exterior cooling chamber 32. Another way to share the same cooling source is by passing the coolant 36 through the capillary lines 40 and the exterior cooling chamber 32 in sequential order. Either way, as long as the exterior and interior cooling can share the same source, it is possible to take the advantage of the single cooling system. The preferred embodiment is to have the coolant passing through the cooling capillaries 40 first and then going through the outside cooling chamber 32 to eliminate the need of high-pressure requirement for the exterior chamber.

C. Injection Device

With the increase in the volume of the separation tube 12 (as compared with CE), more options are available for the injection device 102. In addition to the injection methods employed in conventional CE systems, new choices are also available. One of the new choices is directly injecting samples into the inside of the separation tube 12. Alternatively, samples can be injected into the inlet tip of the separation tube 12.

Injection methods commonly used in traditional CE can also be used here. For example, the hydrodynamic injection can be applied to the inlet end of the separation tube 12. This hydrodynamic pressure difference between the two ends of the separation tube can be generated through either placing a positive pressure on the injection end or by creating a vacuum at the outlet end. As always, we can add electrokinetic injection into this list as well. By using a reservoir 16 like the one shown in FIG. 4D, it is possible to automate the whole injection process.

By using a sampling line 26, it is possible to directly introduce samples into the inside at the injection end (FIGS. 1, 2 and 8). The said sampling line 26 can be a capillary with an OD small enough that it can be inserted into the said separation tube 12 from the injection end to function as an online injector. In one embodiment, an injector 102 along with a six-port injection valve 104 provides a means of injecting samples into the system. The six-port valve 104 is connected to one end of the said sampling line 26. The other end of the sampling line 26 is inserted into the separation tube 12 from the opening end of the reservoir 16 (or the opening of the T 44 or cross union 46). This sampling line 26 can be directly linked to a syringe or syringe pump 112 that serves as a manual injector. This sampling line 26 can also be connected to one of the six-port injection valve 104 of the manual injector or an autosampler 102 (FIG. 8). Another driving equipment, such as a syringe pump, an HPLC pump or a syringe 112, is also attached to the injection valve 104 to push the sample through the sampling line. Alternatively, this sample can be pulled into the separation channel by applying a vacuum at the outlet end from the sample line 26.

In another embodiment, the sampling line 26 passes through the center of the reservoir 6 and extends out of the opposite side of the reservoir 6. A particular embodiment is that the sampling line 26 extends out of the reservoir 6 along with the cooling capillaries 40 from the same hole and then immediately separated from the cooling capillaries 40 after it passes through the opening of the reservoir 6. The sampling line 26 is connected with other devices, such as a syringe or the injection valve 104 of an autosampler 102 for injection.

When properly designed, it is possible to inject samples right at the tip of the inlet end of the separation tube. Specifically, a small narrow channel can be created near the end of the separation tube to allow the insertion of the syringe needle into the inlet tip to accomplish the injection. The said narrow channel can be created by one of two ways. One way is to use a "T" 44 (or cross 46), which allows the cooling capillaries 40 pass through the straight sides of the T 44 while leaving the side opening for sample introduction. The side arm of the T 44 has a small opening that is suitable for this purpose. The other way is to fabricate a small channel when building the whole electrophoresis cartridge 20. The small channel serves the same purpose. Either way, a sampling line 26 can be introduced near the separation tube 12 by either connecting to this side opening of the T 44 (or cross 46) or to the small channel on the fabricated cartridge 20. Again, sample can be either pressurized into the separation channel from behind or be sucked into the channel from the other end.

D. High Voltage Power Supply

The high voltage power supply 10 can be obtained from commercial suppliers, such as Spellman High Voltage (NY), and/or Glassman High Voltage, etc. The major requirement is the power should be sufficiently higher than that of a typical CE power supply, which is 9 Watts (30 kV, 300 $\mu$A). An upper limit of voltage may be, but not limited to 30 kV, which is the same as a typical CE power supply. However, the upper current limit of this power supply should be at least 1 mA and preferably much higher.

E. Detection

The system also includes a detector 28 for monitoring compound separated by the separation tube. The detector 28 can be any common detector employed by high performance liquid chromatography (HPLC) or CE techniques. The most common ones are the UV/Vis detector and LIF detector. More sophisticated detectors such as MS and/or NMR 130 can also be used. Electrochemical detectors can also be used for this system.

The detection can be performed in multiple ways. One is to simply place the separation tube 12 between a light source 106 and a detection element 108 such as a photodiode (FIG. 8). This can easily be achieved by modifying some of the commercial UV/Vis detectors, such as the Themo Spectra (formally Linear) series detectors. The other option is to use fiber optics to bring the source light near the separation tube and use another fiber optics to carry the signal lights into the detector. For sample, two fiber optical cables (such as a 400-$\mu$m core and UV transmittable cable) have been used to construct this detection system.

In another embodiment, a laser beam is introduced onto the separation tube and the fluorescence signals introduced by the laser is detected by a photodiode at 90° from the exciting laser beam.

In another embodiment, the outlet of the separation tube 12 is interfaced with a mass spectrometry (MS) 130 though a post-separation line 30. Special designs were employed to balance the high voltage required for electrospray ionization process (see Examples for details).

In still another embodiment, the outlet of the separation tube 12 is extended for NMR detection.

II. Multiple Separation Tubes System

Owing to the excellent cooling effects of the present invention, multiple separation tubes 12 can be placed in parallel to form arrays. This simultaneous use of many separation tubes 12 in a parallel array increases the overall throughput of the electrophoresis. Multiple separation tubes 12 are analogous to multiple lanes in standard gel electrophoresis except that the separation tubes are totally isolated from each other. Since the interior cooling is placed inside each of the separation tubes 12, these separation tubes 12 are not related to each other providing the detection is also independently designed, such as by fiber optical cables. Thus, it is possible to have as many as possible separation tubes simultaneously. It is not intended that the current invention to be limited by the precise number of the separation tube. Nonetheless, as a consequence of its effectiveness in cooling, the present invention can cool as many as necessary, such as 8, 12, 96, 384, 1536, etc, separation tubes in multiple layer parallel arrays. Each of the separation tubes can be loaded individually or simultaneous and run either in the same anode and cathode buffers 14 with a single power supply 10 or in different buffers with multiple power supplies.

Similar to the single separation tube system, an electrophoresis system with multiple separation tubes can be built based on the sample principles. Similarly, this multiple separation tube based electrophoresis system also include 1) a separation cartridge containing multiple separation tubes for performing electrophoresis; 2) a cooling system to carry away the Joule heat; 3) an injection device for introducing samples into the separation tubes; 4) one or more power supplies capable of delivering sufficient power; and 5) one or more detectors for monitoring compound separated by the separation tubes. Due to the complexity of multiple separation tubes, each of the components has its uniqueness in their design.

A. Multi-tube Cartridge

The separation cartridge 20 for a multiple separation tube system can be built similar to the single tube system. The use of multiple tubes in parallel enhances the throughput of the system. Due to the significant difference in the complexity of making these systems, it can be generally divided into two categories. One is with 12 or less separation tubes and the other is with more than 12 separation tubes. In the first case, the separation tubes can be laid out in parallel in the same plane. The reservoirs can be fabricated on the same plane as well. When the number of the separation tubes is more than 12, the separation tubes have the option of easy staying in a single layer or stacking into multiple layers to accommodate the requirement for a two dimensional geometry of other devices, such as the industrial standard 96-well plate, with the multiple separation tubes. Due to the effective cooling of the present invention, more than 96 tubes may be utilized in parallel arrays as well.

B. Multi-tube Cooling System

The cooling system is also similar to the single tube system except the cooling power needs to be significantly higher than that in a single separation tube system. Considering the high demand, it would be advantageous to use the cooling capillaries 40 in the multiple separation tubes as the evaporator coil as in a typical air conditioning process (FIG. 7).

C. Multi-tube Injection System

The injection device needs to be multi-channel as well to accommodate the new requirements of the separation tube array. For systems with less than 12 channels, commercially available manual multi-channel syringes or automated multi-channel autosamplers can be used for this purpose. Both the sample line 26 and the T 44 option disclosed previously can be used for this multiple separation tube array. For systems containing more than 12 separation tubes, it may be necessary to modify some of the commercially available 96 (or 384) channel liquid handler to achieve the multi-channel injection. Alternatively, it is always feasible to inject multi-channels simultaneously by using multiple sample lines and inject in a way similar to the CE cases.

D. Multi-tube Power Supply

The high voltage power supply used for this multiple separation tube array should be able to handle significantly higher current. Further, if costs permit, each individual separation channel should have individually controlled voltage. In a preferred embodiment, the current in each individual separation tube should be measured separately.

E. Multi-tube Detection System

For multiple tube array system, the detection method can be based either on a photodiode array (PDA) for a single dimensional detection or a charge-coupled device (CCD) for a two dimensional detection. Again, LIF and electrochemical array detection techniques can also be employed for these systems.

III. Slab Based System

In the slab electrophoresis, the separation is accomplished between the two flat plates (glasses or plastics) (FIG. 3D). The traditional slab gel electrophoresis has no efficient way of removing the Joule heat except using excessive amount of coolant, such as cold buffer to circulate around the exterior surfaces to carry the heat away from the gel. Since this method is not very efficient, the electrical field strength in slab gel electrophoresis is kept relatively low. By incorporating in the current invention, the Joule heat can be quickly removed. In such a slab electrophoresis system, it may contain similar devices as in the tube based separation system. The major components are a) a separation cartridge, b) a cooling system, c) an injection device, d) a power supply, and e) a detection system. The power supply can be similar to the multiple separation tube system.

The slab cooling system is similar to the tube based system. The major differences are a) significantly more numbers of cooling capillaries may be needed to fill into the system; and b) the intersection of the system is rectangular rather than a circle. The cooling capillaries are "sandwiched" in the middle of two flat glass plates. These cooling capillaries 40 are tightly packed together forming various structures to efficiently cool the electrophoresis system. Gel, if necessary, can be poured into the space formed between the two glass plates 54 and the outer surface of the cooling capillaries 40. At least one end of the cooling capillaries 40 is connected to a connector 48 that can be pressurized to drive coolant 36 to pass through the cooling capillaries 40.

By inserting cooling capillaries 40 close together in the middle of the flat glasses, the convective flow inside the glasses is reduced. Therefore, electrophoresis can be run without the gel, which makes it possible for detecting the separated analytes on the spot without any chemical pretreatment, such as staining. To be UV transparent, the glass plates 54 have to be UV transparent in order to detect analytes directly.

The power supply 10 and the detection system 28 can be the same as in the multiple separation tube array system. The injection can be accomplished as disclosed above as well. In addition, traditional sample loading combs can also be used for this purpose if a gel is used.

V. Continuous 2-D Electrophoresis System

Figure 10A:
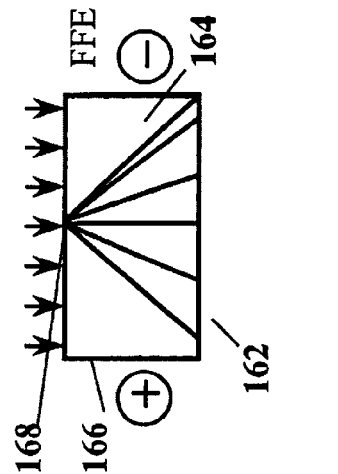
FIG. 10A-C show the views from the front (A), side (B) and top (C) of the continues 2-D system.

When compared to CE, the separation tube 12 involved in a wide bore electrophoresis is significantly larger. However, the overall scale of the most current electrophoresis is still relatively small. Since simultaneous cooling of the electrophoresis system from both inside and the outside is especially efficient in removing Joule heat, it is anticipated that the current invention can also be incorporated into relatively larger scale electrophoresis system for preparative purpose. For example, FIG. 10A is a scheme of a continuous two-dimensional (c2-D) electrophoresis system 160. The c2-D system comprises two major parts for performing separations based on two different, and preferably orthogonal mechanisms. The top part is a rectangular slab electrophoresis 162 (FIG. 10A), which is made of two glass plates 164 similar to traditional slab gel electrophoresis. However, the interior cooling of the current invention is incorporated into this system to enhance the separation efficiency. In addition, this part also serves the purpose of providing samples to the second part of the c2-D system. The most common mode in this part is either FFE or isoelectric focusing (IEF) (FIGS. 10D and 10E), which can be run continuously in this dimension. Electrical field is applied to the two side ends 166 while cooling capillaries 40 can be inserted either parallel or, preferably perpendicular to the electrical field. Another force perpendicular to the electrical force is applied to the separation system simultaneously. This perpendicular force usually comes from a mechanic source, such as a pump. The topside is the sampling end 168. Samples can be introduced from a middle point (for FFE) or any point (for IEF) from starting side. In FFE, samples are introduced continuously from a single point near the middle of the sampling end 168 while in IEF, samples are introduced continuously to the system at any point (or multiple points) on the sampling end 168 (FIGS. 10D and 10E). For FFE, the specific location of the point on sampling end 168 depends on the specific sample and can be adjusted depending on the charges of the samples, such as proteins. Then samples are separated by the electric force while passing through the electrical field under the mechanic force. Samples separated from this first dimension form a series of separated sample bands along a straight line that can be further separated in the second dimension.

Figure 10B:
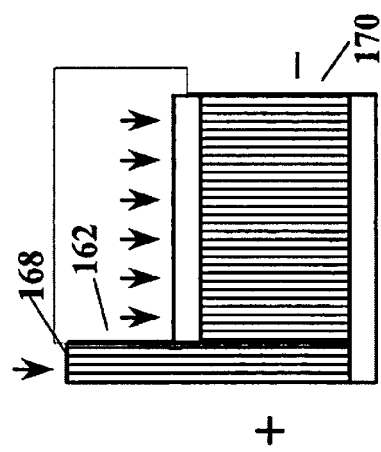
Figure 10C:
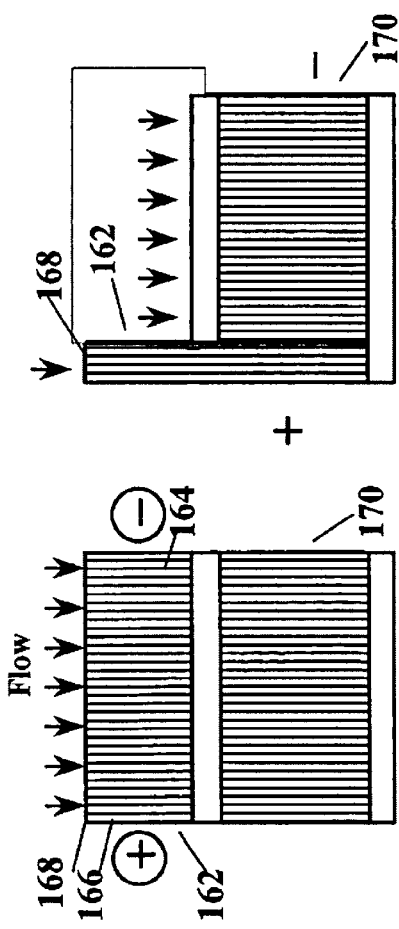
Figure 10D:
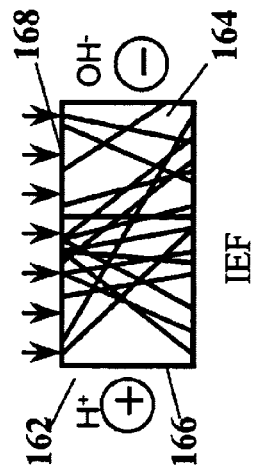
FIG. 10D shows the separation trace in a FFE process.
Figure 10E:
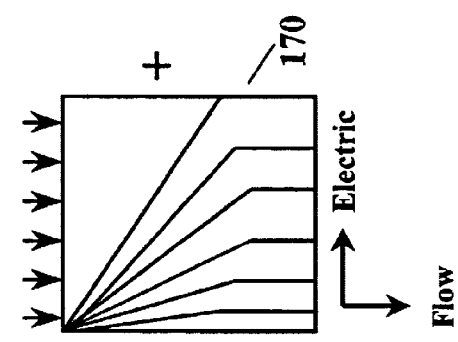
FIG. 10E shows the separation traces of a dynamic IEF process.
Figure 10F:
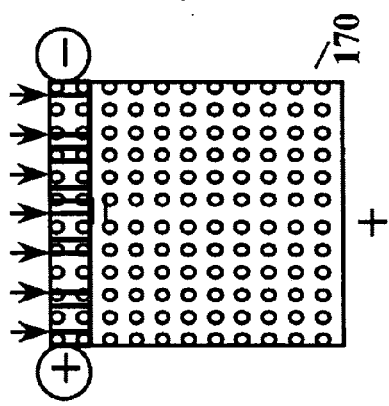
FIG. 10 shows the general principles of a continues 2-D electrophoresis system and the traces of the sample separation in the system.

The bottom part in FIGS. 10A–10C is the second dimension of electrophoresis 170, which allows samples to be separated by a mechanism different from that in the first dimension. This dimension can be either sized based separation, such as SDS-PAGE like separation, chromatographic based or any other mode of separation. Samples after either the IEF or the FFE separation form multiple bands at the inlet of the second dimension 170. These sample bands are further separated in the second dimension under the flow force and the electrical force as shown in FIG. 10F.

The second dimensional separation usually happens in a three dimensional space. The sample bands separated from the first dimension form a line to enter the second dimension from one edge of the 3-D structure. Another electric force perpendicular to this line is applied to separation the sample bands further into more resolved spots. A flow driving by a mechanic force, which can be the same or different from the mechanic force in the first dimension, is applied in the direction perpendicular to the plane formed by the sample line and the electric force. This mechanic force will carry the separated samples to the collecting end for collection. Since the whole process of this separation can be maintained continuously, it is thus suited for preparation purpose.

During the first dimensional separation, the cooling capillaries are aligned parallel to the separation plane but perpendicular to the electric force. In the second dimensional separation, the cooling capillary lines are perpendicular to the plane formed between the electric field and the sample line. In both cases, the cooling capillaries are parallel with the mechanic force as shown in FIG. 10.

The major difference between the c2-D and the conventional 2-D electrophoresis systems is that the separation in the first dimension is actually performed on a two dimensional plane while the second dimensional separation is accomplished in a 3-D space. The added dimension allows the continued operation of the electrophoresis process.

5. Applications of the Current Invention

The present invention provides innovative apparatus, methods and systems that can have broad applications in many different areas, including but not limited to, chemistry, biology, forensic science, food, environment, pharmaceuticals and health care, etc. For example, genomics has predicted that there are more than thirty thousand genes in many biological systems, including human. However, the numbers of known proteins are significantly less than the numbers of genes. As of now, many more proteins still remain unidentified. This is one of the main goals of the current proteomics, which suffers from the lack of suitable tools to reach this goal. One of the two major strategies in current proteomics involves the following technologies: sample preparation, two-dimensional gel electrophoresis separation, gel staining, gel imaging and image analysis (i.e. spot identification), gel cutting, off-line enzyme digestion, sample desalting and transferring, MALDI MS and/or HPLC/MS/MS, etc. The other strategy uses two-dimensional capillary HPLC directly linked to MS/MS. Both strategies rely on the combination of two core technologies. One is a separation technique with high resolution, such as 2-D electrophoresis or 2-D capillary HPLC. The other core technology is a method of providing structural information, such as MS/MS.

The strategy of using 2-D electrophoresis provides the best resolution in separating hundreds or even thousands of proteins. 2-D electrophoresis is the best technique for separating proteins from biological samples that are usually complex mixtures of many proteins. Unfortunately, the current 2-D electrophoresis technique suffers from the following drawbacks. It is tedious to operate, hard to quantify, not reproducible, and almost impossible to automate. The inability for automation has driven people away from electrophoresis and forced people to use the second strategy of using the 2-D capillary HPLC. Although 2-D electrophoresis has the highest separation power among all known separation techniques, people are willing to scarify this to prefer the gain of automation in the second strategy. This fact demonstrates the importance of automation in the whole proteomics project. In addition, the compatibility of the separation technique with another key technology, MS, is also of key importance. Usually, there are several independent steps before samples separated by the 2-D electrophoresis can be introduced into MS. Capillary HPLC, on the other hand, offers the advantage of online compatibility with MS.

The present invention offers the best combination of all for the separation of various proteins, as well as other molecules. First, it is an electrophoretic technique, which is the technology best suited for the separations of proteins and other biopolymers. It is expected that the separation efficiency of this technique will be much higher than that in the capillary HPLC technique. Second, it is much easier to operate as it can be fully automated. The present invention can be operated from sample preparation to MS detection all online; it is possible to perform the analyses of various protein samples un-attended. Third, the size of the separation tube, and thus the amount of samples, is significantly increased (hundreds of fold) or even more from the CE level. This increase makes it perfectly matching the sample requirement for MS. For example, 1 $\mu$L of sample with a concentration of 1 $\mu$M (UV detectable) would be 1 pmol, which is readily detectable by modern MS technology. Fourth, even the volume is significantly increased, the efficiency of the separations can be expected to be similar to that obtained in the current CE technique due to the improved efficiency in heat removal. Fifth, another unique advantage of the current invention is in biological applications where protein samples can maintain their biological activities after the separation. None of the current two strategies in proteomics can maintain the biological activities of proteins after their separations. The retention of biological activities of proteins is important because it is often more important to identify the functions than to simply obtain a new protein itself. Currently, many proteins that match the specific genomic sequence have been found and confirmed by expression may not necessarily have the right biological activities, which are of critical values to many studies in proteomics. On the other hand, if we can obtain the same proteins by separating them directly from their native matrix and maintain their biological activities, it will save a lot of efforts and significantly improve the success rate in finding clinically meaningful targets.

Figure 9:
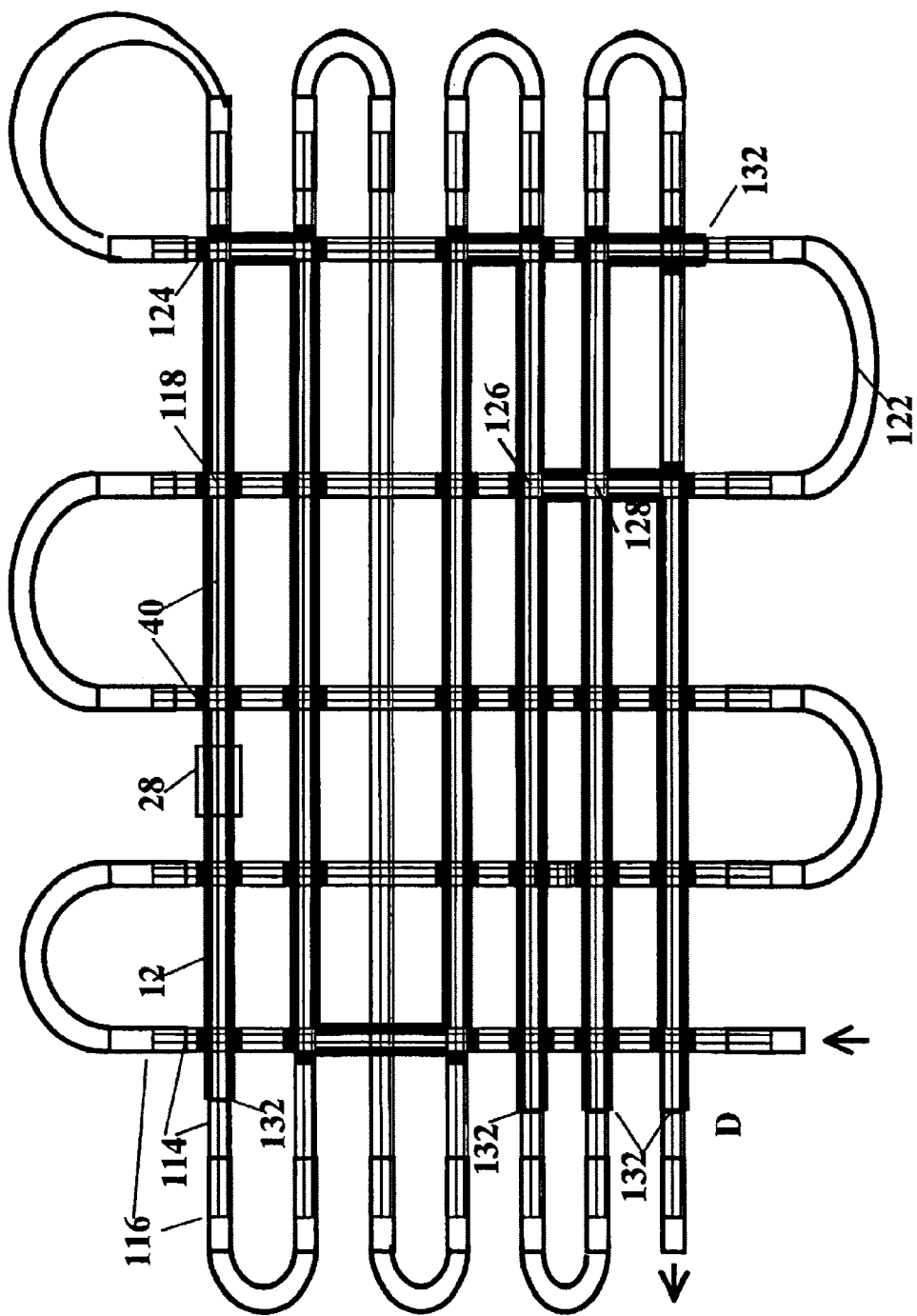
FIG. 9 shows the basic structures of a lab chip incorporated with a network of cooling capillaries for interior cooling. bore electrophoresis system and other instruments, including sample preparation station, fraction collection and mass spectrometry detection.

A typical example of this invention for proteomics and other applications is shown in FIG. 9, which shows that electrophoresis system 100 as described in FIG. 8 in connected online with multiple instruments for potential proteomics and other applications. Before the electrophoresis system 100 is a sample preparation station 120, which process the samples for the electrophoresis system 100. This sample station 120 may either serve as an autosampler 102 itself or transport the processed samples to the autosampler 102 of the high performance wide bore electrophoresis (HPWBE) system. Then, samples are separated by the electrophoresis process, which may be single dimensional or multi-dimensional. The separated samples may be directly introduced into a proper detector 130 or diverged into a fraction collection device 140 for post-separation treatments. Some of the proper detectors 130 are MS and NMR, which can be linked to the electrophoresis system 100 directly. Both of them provide structural information about the separated proteins. Other detectors, such as UV/Vis, LIF, and electrochemical detectors can also be applied here. An optional fraction collection device 140 can be attached to the electrophoresis system 100 to collect the separated components for subsequent analyses or reactions. The post-separation treatments of the collected fractions include digestion by enzyme, desalting, growing crystal, or other further sample preparation procedures to get the samples ready for the subsequent steps, such as MS and/or X-ray analyses. The collected fractions can also be directly submitted for sequencing or biological activity assays. A computer 150 controls the operations of all these components.

EXAMPLES

In this section, an electrophoresis system is provided that includes a separation tube, two buffer reservoirs 16, one or more cooling capillary (or capillaries) 40 made of electrically nonconductive material, one or two connectors 48, an injector 102, a sample, and an electrical source. One end of the tube is placed in contact with the first buffer reservoir, and the other end of the tube is placed in the second buffer reservoir. The cooling capillaries are inserted inside the separation tube and pass through the reservoirs without electrical or fluidic communication with the reservoirs. One end of the cooling capillaries is connected to the coolant through a connector. A detector is placed either online or off line. In the later case, a small capillary line 30 is used to bring samples passing through the detector. Subsequently, high voltage is introduced to the buffer reservoirs.

The method for performing electrophoresis comprises the following steps. First, prepare the experiment by setting up the separation cartridge 20 as described above; adding buffers to the first and the second buffer reservoirs; pushing the buffer through the separation tube to have the first and second ends in fluidic communication with said first and second buffer reservoirs; and connecting the said first and said second buffer reservoirs to an electrical source.

Second, connect the injection sample line to an injector (or autosampler).

Third, connect the detector to the separation tube through one of two ways. One is on-column detection and the other is post-column detection.

The method further comprises introducing a sample into said first end of said separation tube; forcing a gas or liquid cooling medium pass into said cooling capillaries with a pump or a compressor.

Due to the high efficiency of the cooling of the present invention, new, large capacity separation tubes are encompassed by the present invention. In one embodiment, the separation tube has an inner diameter greater than 1000 micrometers. In another embodiment, this separation tube is cylindrical. Alternatively, the separation tube has a polygonal cross-section; and in another embodiment, has cross-section dimensions between 0.1 mm×0.4 mm and 0.1 mm×1 cm. Further, with more cooling capillaries involved, the separation tube can be further increased.

This invention can be incorporated into other systems. For example, this invention can be incorporated into lab chip platform to enable more samples to be separated on a lab chip. Similarly, this invention can be incorporated into slab electrophoresis system to enhance the cooling capability. Further, in still another embodiment, a continuous 2-D electrophoresis can be built by incorporating this invention.

The following examples serve to illustrate certain preferred embodiments and aspects of the present invention and are not to be construed as limiting the scope thereof.

Example 1

Optimization of the Separation Tube and Cooling Capillaries

In a standard CE system, the separation capillaries usually have an ID of 10 to 100 micrometers. This small ID severely limits the amount of samples that can be separated by CE. Due to the efficient cooling of the heat sink contemplated by the present invention, much larger ID electrophoresis channels can be used. While a variety of cross-sectional dimensions of the channel shapes, such as rectangular and square, are contemplated, a circular tube is preferred because of its strong mechanic strength. In one embodiment, the separation tube has an ID exceeding 1000 micrometers, which is readily available from commercial sources. For example, Polymicro Technologies, LLP (Phoenix, Ariz.) has fused silica tubes with an ID of 1 mm and OD of 1.5 mm. GE quartz has various sizes of quarts tubing suitable for the separation tubes. Further, there are several vendors that can provide various sizes of plastic tubing.

While the present invention contemplates a variety of size and number of cooling capillaries as well the size of the separation tube, in this example, the selection of dimensions of a specific separation tube and the cooling capillary bundle is guided based on the following calculations.

a) General Relationship

While it is possible to have a combination of various sizes and shapes of cooling capillaries for the capillary bundle, for simplicity, we use the scenario that the cooling capillaries have the same OD. Assuming the internal radius of the separation tube is R and the external radius of the cooling capillary is r, then, the surface-to-volume ratio (S/V) and the number of cooling capillaries, n, has the following relationship:

$$\frac{S}{V} = \frac{2\pi R + n2\pi r}{\pi R^2 - n\pi r^2} = \frac{2(R+nr)}{R^2 - nr^2} \quad \text{(Eq 1)}$$

when n is 0, S/V is 2/r; when n is 1, S/V is 2/(R-r).

In this system, the surface is the total surface area in contact with the separation buffer including the inner surface of the separation tube and the outer surfaces of all of the cooling capillaries. If the capillaries are circular in cross-section with different ODs, the number of the capillaries, n, and the S/V has a more general relationship, i.e., $$\frac{S}{V} = \frac{2\left(R + \sum_{i=1}^{n} r_i\right)}{\left(R^2 - \sum_{i=1}^{n} r_i^2\right)} \quad \text{(Eq 1a)}$$

It is clear from the above S/V relationship that all three parameters, n, R, and r, affect the final S/V values and they are all inter-related. For example, r should always be smaller than R. Therefore, the overall relationship is quite complicated. Multiple relationships can be obtained when we fix only one specific parameter. For example, we can obtain the same S/V value either by inserting one capillary having a radius (r) of 0.9R or by inserting three capillaries with a radius of 0.5R, i.e. if n=1 and r=0.9R, then S/V=2/(R−0.9R)=20/R; if n=3 and r=0.5R, S/V=2(R+3r)/(R²−3r²)=2×2.5R/0.25R²=20/R. This calculation confirms that there is more than one way of obtaining the same S/V ratio if we only consider cooling effect alone. All of these parameters, R, r, n and S/V should be considered simultaneously in order to optimize the relationships. In order to obtain the one-to-one relationship between the any two parameters, such as S/V and n, it is necessary to fix at least two other parameters, such as R and r values. In order to determine which parameters to fix first, we consider the following factors.

b) Selection of n

From the manufacturing point of view, inserting less capillary is easier. Apparently, inserting a single capillary with a radius of 0.9R is much easier than inserting three capillaries with a radius of 0.5R into the same separation tube with a radius of R. However, using less but larger cooling capillaries has significant drawbacks.

First, in addition to surface-to-volume ratio, we need to consider the effective volume. The ultimate purpose of this invention is the find the most efficient way of increasing the effective sizes of the separation tube, and thus the separation volume, while keeping the Joule heat under control. Inserting a large capillary occupies too much volume from the separation tube leaving little space for sample separation. In the above example, even with the same S/V ratio, the volume remained for actual sample separation with three capillaries (r=0.5R) is 32% more than that using only one larger capillary (r=0.9R), i.e. $(\pi R^2 - 3 \times \pi (0.5R)^2)/[\pi R^2 - 1 \times \pi (0.9R)^2]=(1-3\times 0.5^2)/(1-0.9^2)=1.32$. Based on the consideration of effective volume, it is concluded that multiple smaller cooling capillaries are preferred over a single and larger cooling capillary.

Second, using multiple smaller capillaries is also desirable from the separation perspective. When the cooling capillaries have large ODs, the interstices among these large cooling capillaries are like big channels (cracks). For example, the three cooling capillaries of the 0.5R radius divide the same interstices into four smaller channels with the biggest edge-to-edge distance within any single channel significantly smaller than the edge-to-edge distance in the case of a single inserted cooling capillary of 0.9R radius. At the extreme, when the ID of the separation tube and the OD of the capillary are both sufficiently large, the space between the two tubes is like a flat surface.

Third, if the interstices are too big, the cooling efficiency will be limited. The efficiency of heat dissipation from these big channels is not as high as that from the multiple channels formed between the cooling capillaries with smaller IDs. This is due to the fact that a good part of the buffer is not in the proximity of the cooling capillaries and the Joule heat is not transferred in imminently.

Thus, the optimized situation would have the largest number of relatively small cooling capillaries possible under a specific S/V ratio. In this example, other parameters were decided first before the number of cooling capillaries was determined.

c) Selection of r

Based on the aforementioned theory, a large number of smaller cooling capillaries is the preferred selection when the sample volume and cooling efficiency are considered. However, there are problems with too small capillaries as well. The first issue is the constructional cost. If the diameters of the cooling capillaries were too small, too many capillaries would be needed to fill in and the cost would be high. The second issue is the difficulty in pushing the coolant into the cooling capillaries because it is well known that the pressure drop required for pushing liquid in a tubing is inversely proportional to the multiple power of the radius of the tubing. The third issue is the convenience of making the capillaries. If the diameters of the cooling capillaries were too small, the mechanical strengths would be too weak to be inserted into the separation tube without breakage. It is not the intention to be limited to the specific sizes and dimensions; we first decided to use capillaries with an OD of around 200 μm to construct the cooling capillaries. The OD diameter of 200 μm was selected for multiple reasons. First, when stacked together, the spaces among these 200 μm capillaries, if they are in contact to each other, is reasonably small. Second, an OD of 200 μm gives us enough room to select capillaries with an ID large enough for passing coolant through. Based on the commercial availability and the mechanic strength of the available capillaries, we selected 100 μm ID capillaries as the cooling capillaries.

d) Selection of V and S/V

After the radius of the cooling capillary is chosen, another parameter from the remaining parameters, R, S/V ratio, and n, has to be determined in order to obtain the one-to-one relationship. Yet another parameter, the absolute value of V may also be important in determining these parameters. Since all of these parameters are inter-related and r has been selected already, we can't simply select another parameter and still meet all of the relationships among them.

To simplify the parameter determining process, we chose a reference point first before optimizing these parameters. Since a 50-μm ID capillary can be routinely run under normal airflow as the cooling means, we chose 50-μm ID capillary as the reference point. We made an assumption that at a minimum, the simultaneous cooling as disclosed in this invention should be able to reach the same cooling efficiency as a conventional CE system for a 50-μm ID capillary. Since the S/V value in a 50-μm ID capillary is around 80 mm²/μL (see R. P. Oda and J. P. Landers, Introduction to Capillary Electrophoresis, in Handbook of Capillary Electrophoresis, 2$^{nd}$ Ed., J. P. Landers, Ed., CRC Press, 1997, pp. 1–48.), this value is a good reference point for S/V ratio. At the same time, we chose the volume of this capillary at unit length ($V_0$) as the reference point for the absolute volume. By using this reference points, we can obtain the relationship between the ID of the separating tube (R) and the number of capillaries (n) for the cooling capillary bundle at any preselected S/V ratio and volume of the interstices.

For example, to build a new system with a S/V of 80, the radius R of the separation tube and the number, n, of capillaries each with a radius of r, should be $S/V=2(R+nr)/(R^2-nr^2)=80$. When r=0.1 mm, we have the first R vs. n relationship:

$$R=(1+(1+80\ n)^{0.5})/80 \qquad (Eq.\ 2)$$

At the same time, if the effective volume at unit length, V, in the new system is 100-fold the volume at unit length, $V_0$, of a 50 μm ID open capillary ($r_0$=25 μm), i.e., $V/V_0=(\pi R^2-n\pi r^2)/(\pi r_0^2)=100$ and r=0.1 mm, we obtain the second R vs. n relationship:

$$R=(0.1n+0.0625)^{0.5} \qquad (Eq.\ 3)$$

e) Optimization of R and n

Theoretically, the R and n values can be obtained by solving the two equations together. The calculated results are n=18.6 which is rounded to next integer number, 19. Under this condition, the value of R is 0.5025 mm. Alternatively, we may plot the two equations and find the cross-point on the graph, which gives the same results. These results represent the optimized combination of the number of capillaries (n), the size of the capillaries (r), and the size of the separation tube (R) under one specific set of conditions, i.e. S/V=80, $V/V_0$=100. Of course, the numbers thus determined are just theoretical numbers. If the conditions (i.e. S/V and $V/V_0$ values) change, the optimized values for parameters, r, R, and n will change accordingly. To generalize the optimization process, it is the best to find the optimized combination by seeking the cross point on the graphic plots of the two relationships (Eqs 2 and 3) between the radius of the separation tube (R) and the number of capillaries (n) under a specifically defined values of S/V ratio and volume.

In real experiments, this number may actually change due to two factors. First, the actually available sizes of the separation tube (R) and the cooling capillary (r) may not be perfectly matching the calculated results. Second, the cooling capillaries have specific geometry, it can't use all "free" spaces within the separation tube and thus the actual number of n is always smaller than the calculated one and thus the S/V ratio is actually smaller than the targeted one. On the other side, the actually volume V is larger than the targeted one.

In our experiments, we constructed cooling capillaries using two different types of fused silica capillaries: 100 μm ID and 200 μm OD capillaries supplied by Polymicro Technologies, and 50–100 μm ID and 220 μm OD capillaries supplied by another vendor. Our calculation indicated that a total of 18 capillaries with 220 μm OD should be used. However, due to the difficult in inserting the last few capillaries, we dropped a few capillaries to sacrifice a little cooling efficiency in exchange for operational convenience.

In most of our experiments, we used 15 to 16 capillaries as the cooling capillaries.

Example 2

Electrophoresis Method and Apparatus

The present invention contemplates that the simultaneous cooling can be directly employed with commercially available conventional CE, as well as CE enabled by the heat dissipation capabilities of the disclosed heat sink. Since this cooling system involves more than just simply changing the separation cartridge, most of the commercial CE instrument can't use this cooling system without proper modifications. To fully take the advantages of this disclosed invention, we have modified all five systems: separation cartridge, cooling system, high voltage power supply, sampling system, and the detection system. In this example, we constructed the new wide bore electrophoresis system using conventional components for CE and/or HPLC. Briefly, the new system includes a high voltage direct current (DC) power supply, a separation cartridge containing the separation tube along with the cooling capillaries based on the current invention, buffer reservoirs, a sample injector, and an UV/Vis detector. Two different flow cells were used for this detector. The data was recorded by using an HP 3903 integrator.

The first is to select a suitable power supply. Most of the power supplies in the current CE instruments can only handle a few watts of power, which is not sufficient for this experiment. Due to the high efficiency of the current cooling system, this new power supply needs to be at least 10 times and preferred 100 times more powerful than the power supply in most current CE instruments. This scale of power supply is readily available from commercial sources. For larger systems, more powerful power supplies are needed.

Most of the current CE system has only exterior cooling and is not easy to be modified for incorporating the simultaneous cooling of the present invention. We built the cartridge along with the cooling system from scratch. In this experiment, the cooling system contained all components disclosed in the general description part of this invention. The cooling capillaries were built in the separation cartridge as shown in FIGS. 2 and 6. An HPLC pump was used to pump cold water, which is mixed with ice. A 1/16" stainless steel tubing line was used to transport the cold water and was connected to the cooling capillaries through a union. To avoid leakage at extremely high pressure, a flow rate of less than 10 mL/min was used in most applications and the back-pressure of the system is less than 4000 psi.

For the current measurements, the separation tubes were around 30–40 cm in length while the cooling capillary bundle was about 40–55 cm depending on specific configurations. Various tubes have been used to build the separation tubes. In one embodiment, a fused silica, polyacryl coated, large bore capillary with a 1.0-millimeter inner diameter and 1.5-millimeter outer diameter (Polymicro Technologies, Phoenix, Ariz.) was tested and no detection window was created on the large bore capillary, as the polyacryl coating is transparent. If polyimide coated wide bore capillary is used, it is necessary to burn a window for on-column detection purpose. In another embodiment, plastic tubing having similar ID was used for this current measurement. Specifically, a 1.04 mm ID PMA tubing, which has good optical transparency as compared to some other polymer materials, was used for this measurement. No specific window was created on this separation tube either as it is transparent. In further another embodiment; quartz glass tubing was also used as the separation tube.

There are at least one and preferably two reservoirs in the separation cartridge. In one embodiment, the said reservoirs are totally detached from each other and are linked only through the separation tube (FIG. 2). In another embodiment, the reservoirs are part of the separation cartridge (FIG. 6). The two reservoirs are built on a rectangular flat board. The separation tube is inserted into these two reservoirs through the walls of the reservoirs and the openings of the separation tube remain inside the reservoirs for fluidic communication with the buffers in the reservoirs and for electric communications with the electric power supply. The cooling capillaries passing through the separation tube extend out of the reservoir from the opposite side for connection with the cooling system. The holes on the reservoirs are sealed with proper glue, such as liquid silicone material, to prevent leakage of the buffer solutions.

The cooling capillaries extended out of the reservoirs were connected to the high-pressure coolant line through a connector, which was made of a metal union. The low-pressure end of the cooling capillaries was inserted into plastic tubing and the coolant, water in this experiment, was collected in a waste container.

The middle part of the separation tube was immersed in a rectangular housing, which contained the buffer reservoirs, the exterior cooling chamber, and the detection compartment. The separation tube passed the two end walls of the housing between the two reservoirs. The holes on the walls for the separation tube to pass through were sealed properly to prevent leakage of the coolant in the housing. Ice along with cold water was added into the housing to maintain the low temperature on the outside of the separation tube.

Since the separation tube is tightly mounted with buffer reservoirs, some of the traditional injection methods, such as the hydrodynamic injection weren't convenient to be directly applied without any modification. While there are many other possible ways of introducing samples into the separation tube, we chose the most convenient way in our experiments. We took advantage of the relatively large ID of the separation tube and inserted a sample line into the middle of the separation tube. The sample line we used in this experiment was a fused silica capillary with an ID of 100 $\mu$m and OD of 200 $\mu$m. The other end of the sampling capillary was connected to a micro-injector through a connection union or to a Ryheodyne 6-port injector.

Both on-column detection and post-column detection were evaluated for this system. Unless transparent separation tube and cooling capillaries are used, it was necessary to burn windows for on-column detection purpose. Windows were burned at approximately 5 cm from the outlet end of the separation tube on the polyimide coating for online detection. No window burning was done for post-column detection.

The detector can be a photodiode, a photo multiplier tube (PMT), or even a spectrophotometer, such as an Ocean Optics USB2000. Most of the commercial UV/Vis detectors for HPLC are not suited for on-column detection in our experiments. With some modification, we used the Spectra Focus detectors (Thermo Spectra-Physics, Mountain View, Calif.) for this experiment. In one embodiment, the detection window on the flow cell needs to be widened to accommodate the increase in the diameter of the separation tube with the current invention for more light to pass through. In addition, the detection cartridge had to be made with a larger hole to allow the larger separation tube to pass through for online detection.

In another embodiment, the online detection was accomplished by using one or two fiber optical cables. One of the optical cables was to introduce the light from the light source directly onto the proximity of the separation tube and the other fiber optical cable carried the signal light after passing the separation tube to the detector.

In further another embodiment, the light bulb from the Spectra Focus detector was brought to the proximity of the separation tube without the help of any fiber optic cable. An optical cable carried the signal light to a detector.

Detection can also be accomplished by post-column detections, which has two advantages. One is to avoid the need to burn windows on the polyimide coatings of the cooling capillaries (sometimes even the separation tube). Window burning may weaken the capillary mechanic strength. Window burning may not be necessary if transparent capillaries are used. The second advantage of post-column detection is the relative ease of operation. A common draw back associated with post column detection in CE is band broadening, which is due to the fact that there is no electric potential to maintain the plug flow and keep the analytes from diffusion. By maintaining certain voltage after the separation tube, it is possible to keep the plug flow profile and reduce diffusion. In addition, it is advantageous to maintain certain voltage on the post-column detection capillary. First, when flow from the separation tube reaches the post-column capillary, it will face some flow resistance from the capillary. Second, when MS detection is needed, it is necessary to maintain certain voltage after the separation tube to accommodate the need for electrospray ionization. In general, there are two ways of providing the potential to the post-column segment. It can be provided either by the same power supply or by a different power source. When a single power supply is used, depending on the potential maintained for the extended capillary for detection, there are two possible relationships between the main electrophoresis potential and the post-column potential. One is like a serial connection while the other is like a parallel connection of two resistors, which are the resistance to the liquid flow not electrical flow in the system. In general, the serial connection of the separation tube with the detection capillary corresponds to a situation where one end of the separation tube is at high voltage while the other end is connected to the detection capillary. The remaining end of the detection capillary is at the lowest potential. The parallel connection is that both ends of the two segments the same voltage. Both of the connections are necessary for detection purpose.

In order to determine the voltage needed to overcome the resistance in the detection segment when the two are in serial, we derive the following relationships based on similar strategies for deriving the relationship between electrical potential and the electrical resistance. When separation tube and the detection capillaries are linked in serial, the flow rate, F, is related to the total potential, V, applied onto the whole system including the detection segment, the length, $l_1$ and $l_2$, the intersection areas $S_1$ and $S_2$, and the mobility, $\mu_1$ and $\mu_2$, of the two segments, respectively, i.e.

$$F = \frac{V}{\frac{l_2}{\mu_2 S_2} + \frac{l_1}{S_1 \mu_1}} \quad \text{(Eq. 4)}$$

The flow resistance R in each segment is $l_1/\mu_1 S_1$ and $l_2/\mu_2 S_2$, respectively. Therefore, the total resistance of the two segments in serial is $$R = \frac{l_1}{\mu_1 S_1} + \frac{l_2}{\mu_2 S_2} \quad \text{(Eq. 5)}$$

It can be concluded from these calculations that:

The flow rate inside the separation tube and the detection capillary is related to the overall potential, the physical dimensions (length and surface area) of the segments, and the motilities of the buffer in these two segments;

Assuming there is no fluidic leakage between the separation tube and the detection capillary, the flow rate, F, is constant in the separation tube and the detection capillary. The linear flow rate, v, in each segment is:

$$v_1 = F/S_1 = V/[S_1(l_1/\mu_1 S_1 + l_2/\mu_2 S_2)] = V/(l_1/\mu_1 + l_2 S_1/\mu_2 S_2), \text{ and}$$

$$v_2 = F/S_2 = V/[S_2(l_1/\mu_1 S_1 + l_2/\mu_2 S_2)] = V/(l_2/\mu_2 + l_1 S_2/\mu_1 S_1).$$

Thus, the linear flow rates in each segment can be adjusted by adjusting the various parameters. In a specific system (i.e. both 1 and S are fixed) the linear rate is related to the mobility, which is related to multiple experimental parameters, such as the zeta potential of the surface, the buffer pH, ionic strength, viscosity, etc. However, the mobility of the buffer can be easily determined experimentally. The ratio of the two linear flow rates is $v_1/v_2 = (l_2/\mu_2 + l_1 S_2/\mu_1 S_1)/(l_1/\mu_1 + l_2 S_1/\mu_2 S_2)$.

Only when $l_1 = l_2$ and $\mu_1 = \mu_2$, then, $v_1/v_2 = S_2/S_1$.

The electric field strength in each segment can be calculated as well. For example, $$E_1 = v_1/\mu_1 = V/[\mu_1(l_1/\mu_1 + l_2 S_1/\mu_2 S_2)] = V/(l_1 + l_2 S_1 \mu_1/\mu_2 S_2) \text{ and}$$

$$E_2 = v_2/\mu_2 = V/[\mu_2(l_2/\mu_2 + l_1 S_2/\mu_1 S_1)] = V/(l_2 + l_1 S_2 \mu_2/\mu_1 S_1)$$

In one embodiment, there is a common grounding at the outlet end of the separation tube. A high voltage is applied to the separation tube for electrophoresis. At the same time, another high voltage (~4–5 KV) is applied to the exit end of the detection capillary for electrospray ionization. Since the outlet of the separation tube is connected to the inlet of the detection capillary, buffer only moves in one direction. Since the two electrical field strengths are in opposite directions, the buffer will move following the direction of higher electric field strength. Optionally, it is possible to coat the inner surface of the detection capillary to reverse the electroosmotic flow and actually allowing the flow to move only from the separation tube to the detection capillary.

When the two segments are connected in parallel, the total resistance for a parallel system is $$\frac{1}{R} = \sum_{i=1}^{n} \frac{1}{R_i} = \sum_{i=1}^{n} \frac{\mu_i S_i}{l_i} \quad \text{(Eq. 6)}$$

where n equals 2, $l_1$ and $l_2$ are the lengths of, $S_1$ and $S_2$ the intersection areas of, and $\mu_1$ and $\mu_2$ the mobility of the buffer in the separation tube and the detection tube, respectively. It should be noted that when multiple separation tubes are included in the electrophoresis apparatus, n may be an integer larger than 2, such as 4, 16, 80, 100, etc.

When a single potential is applied to all of the parallel tubes, the total flow rate $F = V/R = V/(1/R_1 + 1/R_2)$. However, if the potentials are different on the separation tube and the detection capillary, the flow in the tube and/or the capillary can be calculated separately using the individual flow resistances. This relationship applies to a real parallel situation, which means the potentials at both ends of the segments are the same. However, in the case of positive MS electrospray, the situation is a little more complicated. The voltage on the exit end of the separation tube (or the exit end of the post-column detection line) varies with several parameters, such as the high voltages provided by the electrophoresis and the MS systems and the relative resistance etc. Two buffer solutions were used for this assay, one was 10 mM borate buffer at pH 9.5 and the other was 10 mM ammonium acetate at pH 7.0. The neutral marker dimethyl sulfone (DMSO) was from Sigma Chemical Co. (St. Luis, Mo.). Green Food Dye, manufactured by McCormick & Co, Inc. (Hunt Valley, Md.), was purchased from a Safeway supermarket. The Green dye contains two major components. One of them is the FD&C Blue No. 1, which is principally the ethyl [4-[p-[ethyl(m-sulfobenzyl)amino]-α-(o-sulfophenyl)benzylidene]-2,5-cyclohexadien -1-ylidene](m-sulfobenzyl) ammonium hydroxide inner salt. The other one is FD&C Yellow No. 5, which is principally 4,5-dihydro-5-oxo-1-(4-sulfophenyl)-4-[4-sulfophenyl-azo]-1H-pyrazole-3-carboxylic acid (CAS Reg. No. 1934-21-0). All solutions were prepared with deionized water.

Example 3

Performance of the Wide Bore Electrophoresis System

The applicability of this invention to the actual electrophoresis can be demonstrated by two different kinds of experimental results. The first kind is to obtain the relationship between the current and the applied voltage to see if it still follows the Ohm law. This kind of experiments demonstrates if the system has adequate cooling capacity and efficiency to take away the Joule heat. The other kind of experiments is to perform actual separation to see if we can obtain good separation results with the new wide bore electrophoresis system incorporated with this invention.

For the first purpose, we evaluated the cooling effect by passing the coolant through the cooling capillaries and monitored the current change as a function of the applied potential. The performance of a specific embodiment using a plastic separation tube is compared with the performance of the same separation tube system without coolant passing through the cooling capillaries. FIG. 10 shows the Ohm plots of the electrophoresis system with and without the coolants passing through the cooling capillaries. The currents were measured by switching the high voltage from low to high and then from high to low. The experimental results demonstrated the following. First, the plot of current vs. voltage is linear when the voltage is relatively low even without cooling. The exposure of the separation system to the room temperature environment is sufficient to remove the Joule heat generated in this stage. FIG. 10 shows that even without coolant passing through the cooling capillaries, current as high as 200 $\mu$A is stable. This indicates that, even without any coolant was used, the fact that the S/V ratio is significantly higher has improved the stability of the system. When the coolant (water at room temperature) passed through the cooling capillaries at a flow rate of 1 ml/min, the Ohm plot is linear up to almost 400 $\mu$A. This is a significant improvement over conventional CE instrument system.

Figure 12:
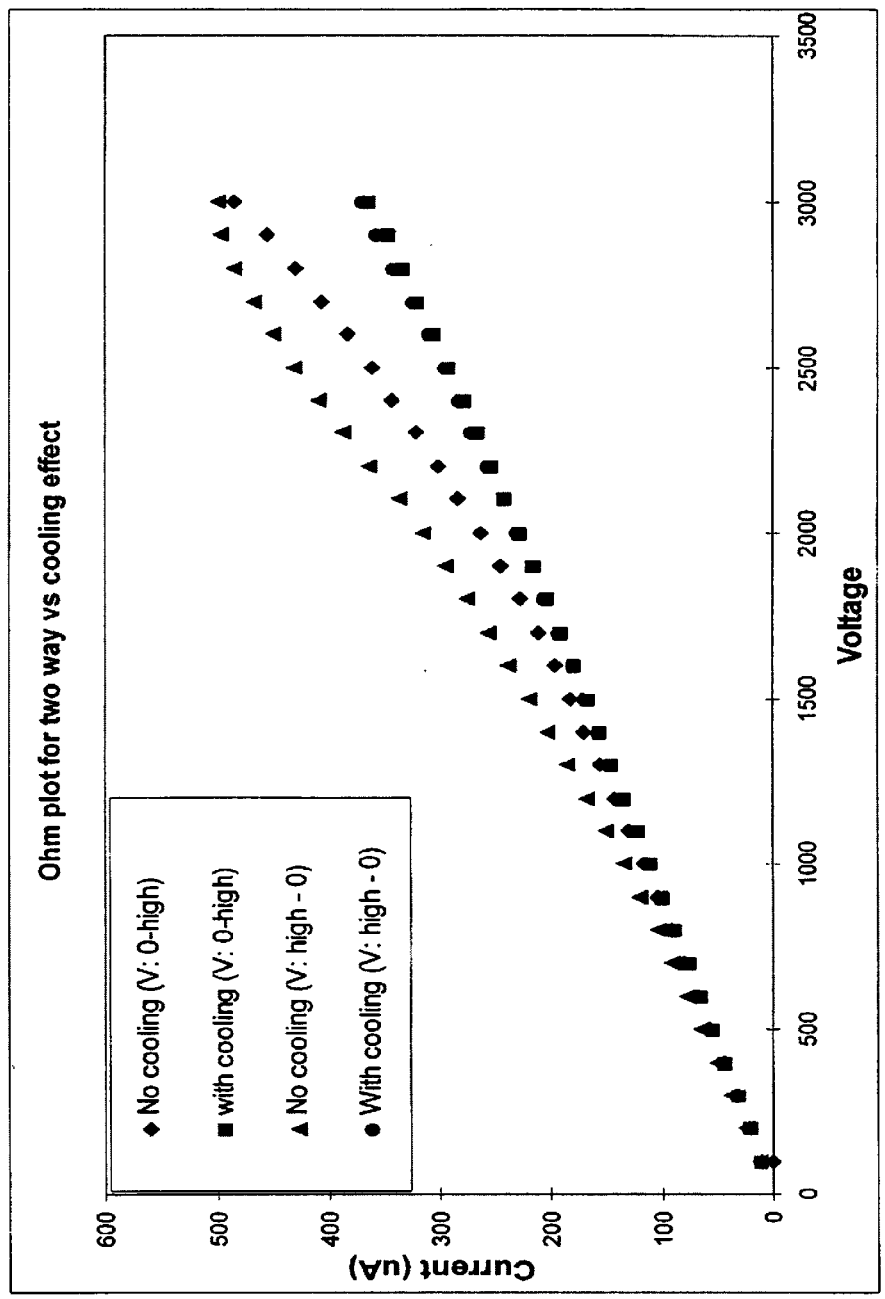
FIG. 12 shows the Ohm plots of one electrophoresis system with and without the coolants passing through the cooling capillaries either from low to high voltage or vise versa.

Second, as the voltage increases, the plot starts to bend toward higher current (FIGS. 10 and 12). System with cooling starts to bend at higher voltage than that without the cooling (FIG. 10). The plots indicated that the interior cooling could significantly improve the heat dispassion and extend the linearity of the Ohm plot.

Third, the plots also show that if the heat is not removed immediately after it is formed, it can be retained within the system as a "memory". After measured the current to a certain level, we reduced the voltage and measured the current as a function of the voltage again. It can be seen that if the current is removed immediately, the reversed path of the current measurement is almost the same as the forward measurement. When the heat was not fully removed, there is a significant difference between the forward and reverse path of the current measurement. If such a cooling is not incorporated, the current is significantly higher when the voltage comes down than when it goes up. The difference is the "residual" current, which is resulted from the accumulated heat and can be reduced to the minimum at low voltage. These results demonstrate that the cooling does remove some Joule heat from the system.

Forth, the effectiveness of the cooling is related to the temperature of the coolant. Cold coolant is more efficient in removing the Joule heat.

Figure 11:
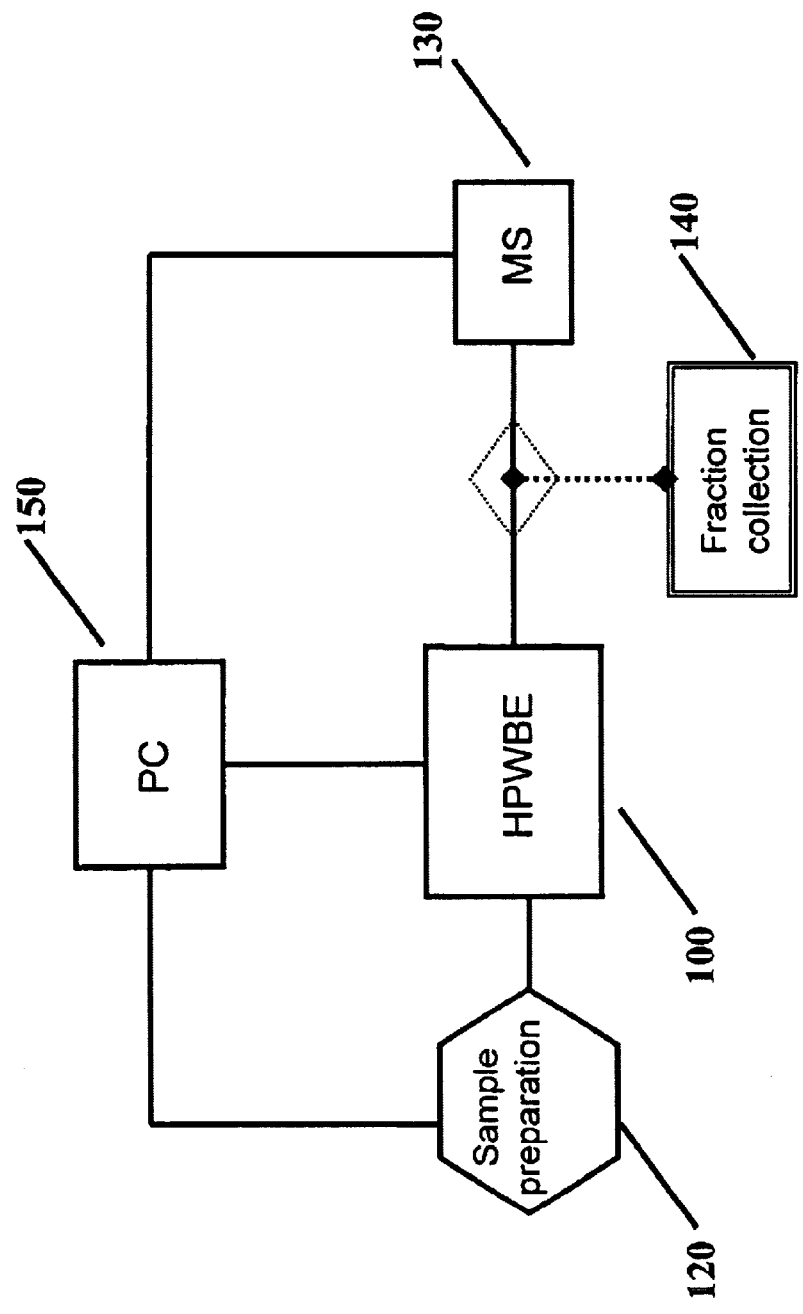
FIG. 11 is a scheme showing the connection between the high performance wide bore electrophoresis system and other instruments, including sample preparation station, fraction collection and mass spectrometry detection.

Fifth, the effectiveness of the cooling also related to the flow rate of the coolant passing through the system. Higher flow rate removes more heat (FIG. 11). Thus, higher cooling efficiency is achieved at high flow rate of the coolant with low temperature coolant.

The following are two examples of actual separation cartridge in our studies. The first one is a plastic separation tube while the second one is a quartz tube with high flow rate. The analysis of the first experiment gives some insights into the system and provides the basis for further improvement.

A. Performance in a Plastic Separation Tube

1) Hear Generation ($Q_g$)

Initially, the maximum voltage we could apply to the system was 4000 V while the maximum current was around 400 μA. The heat generated, $Q_g$, is expressed as $$Q_g = N = IV = 4000 \times 400 \ \mu A = 1.6 \ J/s = 96 \ J/min$$

where N is the power (Joule/sec), I is the current (A), and V is the voltage (V). If no cooling, this heat is enough to heat the buffer system and raise the temperature to "ΔT" degree:

$$Q_g = C_p m \ \Delta T \qquad \text{(Eq. 6)}$$

where $C_p$ is the buffer heat capacity, which is 4.18 J/g.k, and m is the mass of the buffer, ΔT is the temperature raised. The mass in our experiment system consisting of one 1-mm ID separation tube inserted with 16 capillaries of 220 μm OD is: $m = V \times D = \pi(R^2 - nr^2)DL = 3.1416 \times [(0.05 \ cm)^2 - 16 \times (0.011 \ cm)^2] \times 1 \ g/cm^3 \times 40 \ cm = 0.071 \ g$. Thus, the temperature rise was $\Delta T = Q_g/C_p m = (1.6 \ J/s)/(4.18 \ J/g.k \times 0.071 \ g) = 5.39 \ k/s$. This result indicates that if the heat is not removed, the temperature will increase at a rate of 5.39 degree per second! For a buffer system with mobility of $6 \times 10^{-4} \ cm^2/Vs$, under 100 V/cm (4000 V over 40 cm), the velocity of the buffer movement is $6 \times 10^{-4} \ cm^2/Vs \times 100 \ V/cm = 0.06 \ cm/s$. In one-minute period time, the buffer moves 3.6 cm. This is equivalent to have a total length of 40+3.6=43.6 cm, the temperature increase within this one-minute period time is:

$$\Delta T = Q_g/C_p m = (60 \ s \times 1.6 \ J/s \times 40 \ cm)/(4.18 \ J/g.k \times 43.6 \ cm \times 0.071 \ g) = 297 \ k/min$$

which is more than enough to bring the buffer to boiling. However, since there is always some kind of heat transferring exists, the buffer will lose some of the heat during the process.

2) Heat adsorption ($Q_g$)

The same equation (Eq. 6) can be used to calculate the capacity that the coolant can carry away, i.e. $Q_a = C_p \ m \ \Delta T$, where $C_p$ is the thermal capacity of the coolant, which is 4.18 J/g.k for water; m is the mass of the coolant; and ΔT was the temperature increase of the coolant after adsorbing the heat. For example, in our experiment, the flow rate was 1.5 ml/min, the mass of the coolant water was 1.5 g/min. Assuming coolant temperature increased 20° C. after passing through the system by starting at zero degree (ice water) to reach room temperature (assuming 20° C.), the total heat it absorbed was:

$$Q_a = 4.18 J/g.k \times 1.5 g/min \times \Delta T = 4.18 J/g.k \times 1.5 \ g/min \times 20 \ k = 125.2 J/min$$

Thus, the cooling water at a flow rate of 1.5 ml/min has a maximum capacity of carrying away 125.2 J/min, or 2.09 J/s if the temperature can increase 20° C. This is larger than the heat actually generated and should therefore be sufficient to remove the Joule heat. However, the experimental results indicated that the heat was not fully removed, which indicated that the heat transfer efficiency is not ideal. Therefore, system with higher cooling efficiency is needed.

3) Heat Transfer Potential

In general, there are three kinds of heat transfer, conduction, convection and radiation. Unless the temperature difference is very high, radiation is usually less important. Since the coolant is physically separated from the high temperature buffer, convection is not significant in this system either. Therefore, the main means of heat transfer involved in this system is conduction.

According to Fourier's law of Conduction, the rate of heat transfer ($Q_c$) is:

$$Q_c = -kA(dT/dx) \qquad \text{(Eq. 7)}$$

where k is the conductance of the material, A is the surface area. If the conduction of the heat is through a cylindrical wall, then $$Q_c = 2\pi k L (T_1 - T_2)/\ln(r_2/r_1) \qquad \text{(Eq. 8)}$$

where $T_1$ and $T_2$ are the temperature of the inside surface and outside surface of the wall, respectively; $r_1$ and $r_2$ are the radii of the interior and exterior surfaces, respectively. The thermal resistance of the cylinder wall (R) is $$R = (T_1 - T_2)/Q_c = \ln(r_2/r_1)/2\pi k L \qquad \text{(Eq. 9)}$$

The conductance of silica tube is 0.6 J/s.k.m, the ID radius was 50 μm and the length was 55 cm, assuming the temperature between the buffer and the coolant was 40 k, then $$Q_c = 2 \times 3.14 \times 0.55 \ m \times 0.6 \ J/s.k.m \times 40 \ k / \ln(500/50) = 82.9/\ln(500/50) \ J/s.$$

Thus, a single cooling capillary has the potential of carrying away of 36.0 J/s if the water passing through the capillary were heated to the same temperature. This number is far larger than the total heat generated at 96 J/min. With a total of 16 capillaries, this system had the potential of carrying away 576 J/s. Thus, the surface area of the 16 capillaries should be sufficient to remove the all of the heat generated. However, the experimental results indicated that there might be other factors, such as the heat transfer rate, that affected the experimental results.

4) Heat Transfer Rate (from Buffer to Coolant) (g)

If the heat can be fully removed, it is necessary to have a heat transfer rate (q) of $$q = Q_g/(n\pi dL) = 1.6 J/s/(16 \times 3.14 \times 100 \times 10^{-6} m \times 0.4 m) = 796 J/s.m^2$$

For a laminar flow in a pipe with a constant heat transfer rate, q, the Nusselt number is 4.364.

$$N_u = qd/[k(Tw - T_{av})] = 4.364 \qquad \text{(Eq. 10)}$$

where d is the ID of the capillary, i.e. d=100 μm, $$Tw - T_a 32 \ qd/4.364 * k = 796 J/s.m^{2 \times}(100 \times 10^{-6} m)/(4.364 \times 0.6 J/s.m.k) = 3.04 \times 10^{-2} k.$$

Therefore, the temperature rise of the coolant upon leaving the cooling capillary is:

$$T_{out} - T_{in} = 4 \ qL/\rho C_{p, \ av} V_{av} D = 4 \times 796 \ J/s.m^2 \times 0.4 \ m/[(9.98 \times 10^2 \ kg/m^3) \times (4.182 \times 10^3 \ J/kg.k) \times (0.177 \ m/s) \times (1 \times 10^{-4} \ m)] = 1273.6/73.87 \ k = 17.2 \ k$$

Unless the coolant temperature is very low as compared with the temperature of the buffer, this kind of heat transfer rate is hard to achieve. Thus, better cooling system is needed. There are many ways of improving the ability and efficiency of the heat exchange in the system. Among the various means of cooling, the easiest ways of achieving this goal is either to increase the flow rate or to improve the heat exchange efficiency by using different materials. In our experiment, we used quartz separation tube to replace the plastic tubes used in this experiment. We also increased the flow rate of the coolant passing through the cooling capillaries.

B) Performance in Quartz Separation Tube

In this preliminary experiment, we maintained a flow rate of the coolant at 5 mL/min to avoid the risk of breaking the seal in the coolant connector. Better cooling efficiency can be achieved if the cartridge is further improved. FIG. 12 is the result obtained from a separation cartridge using 1 mm ID quartz tube with a total length of 30 cm. As shown in FIG. 12, the current and the voltage follow a simple linear relationship (Ohm's law) when the voltage is relatively low. However, the current starts deviating from the linear curve when the voltage is increased to certain level. Under the specific experimental conditions as described above, the bending point is near 1 mA of current, which is at least several fold higher than the limit of most current CE instruments. This turning point was achieved at 8000 voltages, which corresponding electric field strength of more than 250 V/cm. Therefore, the electrophoresis is under conditions similar to conventional CE.

As part of this experiment, we intentionally increased the voltage and monitored the effect of the system at high current. When the current reached more than 3 mA level, we noticed a very interesting phenomenon. Unlike a typical CE system, where the formation of a small bubble would cut the current and bring the electrophoresis down, this wide bore electrophoresis system had quite stable current even through the liquid inside the separation tube was boiling. We noticed that there was always some liquid remaining underneath the air bubble. The electrical communication was maintained through this liquid. Therefore, large bore electrophoresis is more rugged and is less subjective to the breakdown of the current.

C) Separation Results

Figure 13:
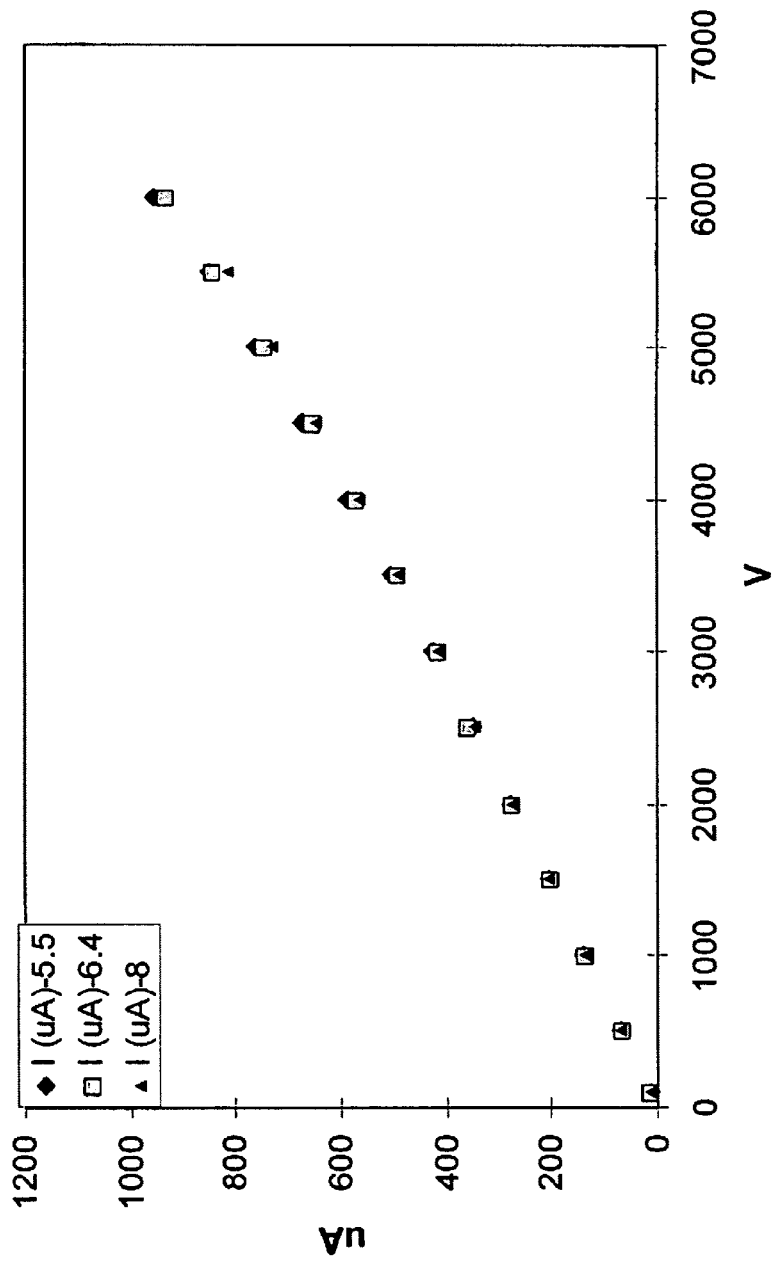
FIG. 13 shows the Ohm plots at different flow rates of the coolant passing through the cooling capillaries.
Figure 14A:
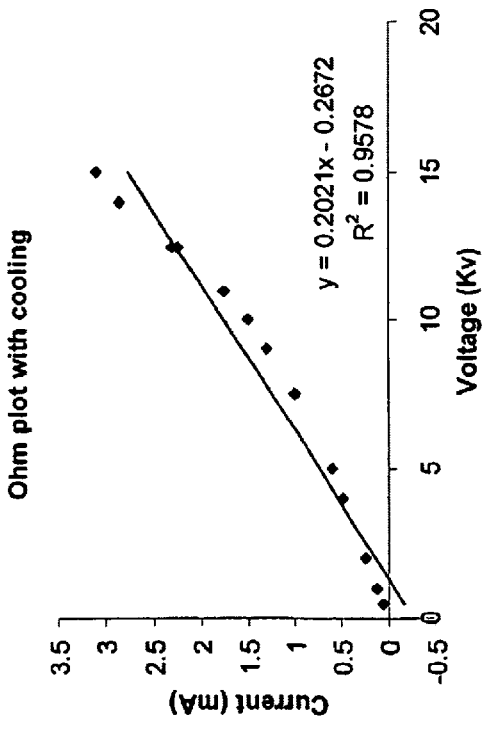
FIG. 14A is the Ohm plot for the whole range evaluated.
Figure 14B:
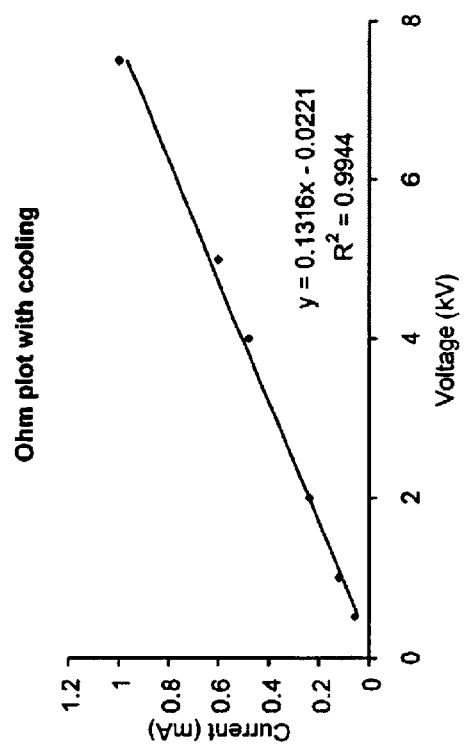
FIG. 14B shows the linear portion of the Ohm plot.

FIG. 13 is the electropherogram showing the separation of the two major ingredients in Green food dye, FD&C Blue No. 1 and FD&C Yellow No. 5. It can be seen from the data that these two dyes were separated very well in this wide bore electrophoresis system.

The above experimental results demonstrated that by using the methods, apparatus and system of the present invention, it is possible to run the electrophoresis at much higher current in a much larger separation tube without the concern of the Joule heat problem. The current experiment was not performed under the best possible conditions. It is anticipated that much more efficient cooling can be achieved if the conditions are further optimized.

Further, the separation of FD&C Blue No. 1 and FD&C Yellow No. 5 demonstrated that this system is capable of performing electrophoretic separations with high efficiency.

What is claimed is:

1. An electrophoresis apparatus for separating analytes in a sample, comprising:
    an electrophoresis chamber comprising a cathode, an anode and a housing;
    a separation chamber having an average inner cross-section of at least 1000 micrometers and positioned within the housing and comprising an inlet end, an outlet end, and one or more cooling capillaries in the form of tubes positioned inside the separation chamber such that the longitudinal axis of at least one of the cooling capillaries is parallel to the direction of electric current flow from the anode to the cathode, wherein the ends of the cooling capillaries are adapted to be coupled to a cooling device that allows cooling medium to pass through the cooling capillary; and
    a cooling device coupled to either one or both ends of the cooling capillary or capillaries through a connector having a mechanic strength tolerable to a pressure of at least 10 psi.

2. The apparatus of claim 1, wherein the separation chamber is a tube or adopts a triangular, square, rectangular, or polygonal box shape.

3. The apparatus of claim 1, wherein the separation chamber is a tube having a circular cross-section.

4. The apparatus of claim 1, wherein the separation chamber is made of an electronically non-conductive material.

5. The apparatus of claim 4, wherein the electronically non-conductive material is selected from the group consisting of glass, quartz, fused silica, and polymer.

6. The apparatus of claim 5, wherein the polymer is selected from the group consisting of Teflon®, polycarbonate, polymethylmethacrylate (PMMA) and silicone.

7. The apparatus of claim 1, wherein the interior of the separation chamber is coated with a chemical layer, especially a hydrophilic layer.

8. The apparatus of claim 7, wherein the hydrophilic layer is polyacrylamide or polyvinyl alcohol or epoxy.

9. The apparatus of claim 1, wherein the cross-section of the one or more cooling capillaries is circular and having an inner diameter between as 10–1,000 micrometers and an outer diameter between 20–1,500 micrometers.

10. The apparatus of claim 9, wherein the one or more cooling capillaries has an inner diameter between 50–500 micrometers and an outer diameter between 100–1,000 micrometers.

11. The apparatus of claim 1, wherein the cooling capillary is made of an electronically non-conductive material.

12. The apparatus of claim 11, wherein the electronically non-conductive material is selected from the group consisting of glass, quartz, fused silica, and polymer.

13. The apparatus of claim 12, wherein the polymer is selected from the group consisting of Teflon®, polycarbonate, polymethylmethacrylate (PMMA) and silicone.

14. The apparatus of claim 1, wherein the separation chamber further comprises one or more solid rods that is electronically non-conductive and positioned inside the separation tube with the longitudinal axis parallel to the direction of electric current flow from the anode to the cathode.

15. The apparatus of claim 1, wherein the separation chamber further comprises one or more open tubes that are made of electronically non-conductive material and positioned inside the separation tube with the longitudinal axis parallel to the direction of electric current flow from the anode to the cathode, the open tubes being adapted to be coupled to the cooling device that allows the cooling medium to pass through the open tubes.

16. The apparatus of claim 1, where the separation chamber further comprises gel or other additives capable of conducting electrophoresis.

17. The apparatus of claim 16, where the gel or other additives is agarose or polyacrylamide or polyethylene glycol.

18. The apparatus of claim 1, wherein cooling device comprises a cooling reservoir containing the cooling medium.

19. The apparatus of claim 18, wherein the cooling medium is selected from the group consisting of chilled water, water-glycerin solution, liquid nitrogen, and fluorochemicals.

20. The apparatus of 18, claim wherein the cooling medium is ice or dry ice.

21. The apparatus of claim 18, wherein the cooling medium is a cooling gas.

22. The apparatus of claim 21, wherein the cooling gas is selected from the group consisting of air, nitrogen gas, ammonia, and carbon dioxide.

23. The apparatus of claim 1, wherein the cooling device is an air conditioner.

24. The apparatus of claim 1, wherein the connector has a mechanic strength tolerable to a pressure of at least 1000 psi.

25. The apparatus of claim 1, wherein the junction between the connector and the end of cooling capillary includes a means for sealing the junction.

26. The apparatus of claim 1, wherein the electrophoresis chamber further comprises a first buffer reservoir and a second buffer reservoir positioned within the housing and coupled to the cathode and anode, respectively.

27. The apparatus of claim 1, wherein the electrophoresis chamber further comprises an exterior heat sink positioned within the housing and configured to contact the exterior surface of the separation chamber to further cool down the separation tube during electrophoresis.

28. The apparatus of claim 27, wherein the exterior heat sink is a liquid bath in which the separation chamber is immersed.

29. The apparatus of claim 21, further comprising: an injection device for introducing a sample into the separation chamber and coupled to the inlet end of the separation chamber.

30. The apparatus of claim 29, wherein the injection device is a syringe or an autosampler.

31. The apparatus of claim 1, further comprising: a high voltage power supply, which provides at least 1 milliampere of electric current during electrophoresis.

32. The apparatus of claim 1, further comprising: a detection device for detecting the presence and/or amount of analytes in the sample separated by electrophoresis.

33. The apparatus of claim 32, wherein the detection device includes a light source and a light-sensing device.

34. The apparatus of claim 33, wherein the light source is a UV-Vis light source and/or a laser.

35. The apparatus of claim 33, wherein the detection device further includes a first fiber optics to transmit light to the separation chamber and a second fiber optics to receive light passing through the separation chamber or emitted from the analytes in the sample.

36. The apparatus of claim 32, wherein the detection device is coupled to the outlet end of the separation chamber to detect the separated analytes released therefrom.

37. The apparatus of claim 32, wherein the separation chamber further comprises a detection tube coupled to the outlet end of the chamber capable of guiding the analytes in a separation buffer released from the separation tube into a flow cell for detection.

38. The apparatus of claim 1, wherein the outlet end of the separation chamber is adapted to be coupled to an analytical instrument for further characterization of the analytes in the sample that are separated by electrophoresis.

39. The apparatus of claim 38, wherein the analytical instrument is an instrument for characterizing the analytes with a technique selected from the group consisting of mass-spectroscopy, nuclear magnetic resonance (NMR) spectroscopy, crystallography, chromatography, and electrophoresis.

40. A method for separation of analytes in a sample by electrophoresis, comprising the steps of:
providing an electrophoresis apparatus which comprises an electrophoresis chamber comprising a cathode, an anode and a housing, and a separation chamber having an average inner cross-section of at least 1000 micrometers and positioned within the housing and comprising an inlet end, an outlet end, and multiple cooling capillaries in the form of tubes positioned inside the separation chamber such that the longitudinal axis of at least one of the cooling capillaries is parallel to the direction of electric current flow from the anode to the cathode, wherein the end of the cooling capillary is adapted to be coupled to a cooling device;
applying an electrophoretic potential to the inlet end and the outlet end of the separation chamber;
delivering cooling medium inside the cooling capillaries through the cooling device;
cooling the separation chamber through the cooling capillaries during the electrophoresis;
detecting the presence and/or amounts of the analytes in the sample, wherein the analytes are detected after released from the outlet end of the separation chamber, wherein the separation chamber is a separation tube and the outlet end of the separation tube is coupled to a detection tube or capillary; and
applying an electrophoretic detection potential to the detection tube to reduce the diffusion of the analytes being released from the separation chamber.

41. The method of claim 46, wherein the electrophoretic potential and the detection potential are applied serially such that the voltage at the inlet end of the separation tube is the highest; and the voltage at the outlet end of the separation tube lower and the voltage at the exit of the detection tube or capillary lowest.

42. The method of claim 40, wherein the total resistance of the separation tube and the detection tube or capillary is determined based on the general formula:

$$R = \frac{l_1}{\mu_1 S_1} + \frac{l_2}{\mu_2 S_2}$$

where $l_1$ and $l_2$ are the lengths of, $S_1$ and $S_2$ the intersection areas of, and $\mu_1$ and $\mu_2$ the mobility of the buffer in the separation tube and the detection tube (or capillary), respectively.

43. The method of claim 40, wherein the electrophoretic potential and the detection potential are applied in parallel.

44. The method of claim 43, wherein the total resistance of the separation tube and the detection tube or capillary is determined based on the general formula:

$$\frac{1}{R} = \sum_{i=1}^{n} \frac{1}{R_i} = \sum_{i=1}^{n} \frac{\mu_i S_i}{l_i}$$

where n equals 2, $l_1$ and $l_2$ are the lengths of, $S_1$ and $S_2$ the intersection areas of, and $\mu_1$ and $\mu_2$ the mobility of the buffer in the separation tube and the detection tube, respectively.

45. The method of claim 40, further comprising the step of collecting the analytes in the sample separated by the electrophoresis.

46. The method of claim 40, further comprising the step of analyzing the analytes in the sample separated by the electrophoresis by a technique selected from the group consisting of mass-spectrometry, nuclear magnetic resonance (NMR) spectroscopy, crystallography, chromatography, and electrophoresis.

47. The method of claim 40, wherein the analytes in the sample are small molecules.

48. The method of claim 40, wherein the analytes in the sample are macromolecules selected from the group consisting of oligosaccharides, polysaccharides, deoxyribonucleosides and analogs, ribonucleosides and analogs, deoxyribonucleotides and analogs, ribonucleotides and analogs, oligonucleotides, DNAs, RNAs, amino acids, peptides, proteins, antibodies, and radio-isotope or fluorescence-labeled molecules thereof.

49. The method of claim 40, wherein the sample is in a form of solution, suspension, cell lysate, or homogenized tissue.

50. The method of claim 40, wherein the separation chamber is substantially free of electrophoresis gel.

* * * * *